US006307037B1

(12) United States Patent
Gaffney et al.

(10) Patent No.: US 6,307,037 B1
(45) Date of Patent: Oct. 23, 2001

(54) FUNGAL TARGET GENES AND METHODS

(75) Inventors: Thomas Deane Gaffney, Chapel Hill; Albert Flavier, Raleigh; Michelle M. Cloyd Kirksey, Durham, all of NC (US); Peter Phillippsen, Riehen (CH); Frederick Dietrich, Durham, NC (US); Jurgen Wendland, Lorrach (DE); Paul Bernasconi, Chapel Hill; Kimberly White, Durham, both of NC (US); Witold Filipowicz, Riehen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/625,188

(22) Filed: Jul. 21, 2000

(51) Int. Cl.⁷ .......................... C07H 21/04; C12N 15/63; C12N 1/21; C12N 1/14; C12N 1/16
(52) U.S. Cl. .................. 536/23.1; 536/24.1; 435/320.1; 435/252.3; 435/254.11; 435/254.2
(58) Field of Search .................................. 536/23.1, 24.1; 435/320.1, 252.3, 254.11, 254.2

(56) References Cited

PUBLICATIONS

Irie et al., Molecular And Cellular Biology, 13(5): 3076–3083 (1993).
Cid et al., Microbiological Reviews, 59(3): 345–386 (1995).
Soler et al., Molecular Microbiology, 17(5): 833–842 (1995).
Paravicini et al., Molecular Gen. Genet. 251: 682–691 (1996).
Zhang et al., Archives of Biochemistry and Biophyscis, 304(1): 133–143 (1993).
Jennings et al., Proc. Natl: Acad. Sci., 88: 6038–6042 (1991).
Fegueur et al., Current Genetics, 20: 365–372 (1991).
Ortiz de Montellano et al., Biochemistry 16(12): 2680–2685 (1977).
Mookhtiar et al., The Journal of Biological Chemistry, 269(15): 11201–11207 (1994).
Barrett–Bee et al., Acta Biochimica Polonica, 42(4): 465–480 (1995).
Grabowska et al., FEBS Letters, 434: 406–408 (1998).
Kennedy et al., Biochimica et Biophysica Acta, 1445: 110–122 (1999).
Nakanishi–Shindo et al., The Journal of Biological Chemistry, 268(35): 26338–26345 (1993).
Nagasu et al., Yeast, 8: 535–547 (1992).
Nakayama et al., The EMBO Journal, 11(7): 2511–2519 (1992).
Romero et al., The Journal of Biological Chemistry, 264(4): 1946–1950 (1989).
Romero et al., Glycobiology, 4(2): 135–140 (1994).
Lehle et al., FEBS Letters, 370: 41–45 (1995).
Verostek et al., Glycobiology, 5(7): 671–681 (1995).

Mondesert et al., Genetics, 147: 421–434 (1997).
Nakayama et al., FEBS Letter, 412:547–550 (1997).
Lussier et al., Biochimica et Biophysica Acta, 1426: 323–334 (1999).
Bateman et al., Nucleic Acids Research, 27(1): 260–262 (1999).
Irie et al., Molecular and Cellular Biology, 14(5): 3150–3157 (1994).
Cade et al., Molecular and Cellular Biology, 14(5): 3139–3149 (1994).
Leberer et al., The EMBO Journal, 13(13): 3050–3064 (1994).
Ko et al., Journal of Bacteriology, 176(16): 5181–5183 (1994).
Wu et al., The Journal of Biological Chemistry, 270(22): 13171–13178 (1995).
Carman et al., The Journal of Biological Chemistry, 271(23): 13293–13296 (1996).
Hashida–Okado et al., Molecular Gen. Genet., 251: 236–244 (1996).
Nagiec et al., The Journal of Biological Chemistry, 272(15): 9809–9817 (1997).
Bender et al., Yeast, 8: 315–323 (1992).
Bender et al., Molecular and Cellular Biology, 11(3): 1295–1305 (1991).
Bender et al., Proc. Natl. Acad. Sci. USA, 86:9976–9980 (1989).
Miyamoto et al., Gene, 54: 125–132 (1987).
Coleman et al., Molecular and Cellular Biology, 6 (12): 4516–4525 (1986).
Ohya et al., Journal of General Microbiology, 132: 979–988 (1986).
Ohya et al., Journal of Bacteriology, 165(1): 28–33 (1986).
Sloat et al., The Journal of Cell Biology, 89: 395–405 (1981).
Zheng et al., The Journal of Biological Chemistry, 269(4): 2369–2372 (1994).
Ziman et al., Yeast, 10: 463–474 (1994).
Zheng et al., The Journal of Biological Chemistry, 270(2): 626–630 (1995).
Simon et al., Nature, 376: 702–705 (1995).
Zhao et al., Molecular and Cellular Biology, 15(10): 5246–5257 (1995).
White et al., Genetics, 147: 43–55 (1997).
Douglas I. Johnson, Microbiology and Molecular Biology Reviews, 63(1): 54–105 (1999).

(List continued on next page.)

*Primary Examiner*—Robert A. Schwartzman
*Assistant Examiner*—Katharine F Davis
(74) *Attorney, Agent, or Firm*—Bruce Vrana

(57) ABSTRACT

The invention relates to genes isolated from *Ashbya gossypii* that code for proteins essential for normal fungal growth and development. The invention also includes the methods of using these proteins to discover new fungicides, based on the essentiality of the gene for normal growth and development. The invention can also be used in a screening assay to identify inhibitors that are potential fungicides.

16 Claims, No Drawings

OTHER PUBLICATIONS

Ziman et al., Molecular and Cellular Biology, 11(7), 3537–3544 (1991).
Johnson et al., The Journal of Cell Biology, 111: 143–152 (1990).
Adams et al., The Journal of Cell Biology, 111: 131–142 (1990).
Miller et al., Molecular and Cellular Biology, 142(2): 1075–1083 (1994).
Ziman et al., Molecular Biology of the Cell, 4: 1307–1316 (1993).
Ziman et al., Yeast 10: 463–474 (1994).
Stevenson et al., Genes & Development, 9: 2949–2963 (1995).
Mosch et al., Proc. Natl. Acad. Sci., 93: 5352–5356 (1996).
Hart et al., The EMBO Journal, 15(12): 2997–3005 (1996).
McCallum et al., The Journal of Biological Chemistry, 271(36): 21732–21737 (1996).
Akada et al., Genetics, 143: 103–117 (1996).
Erickson et al., The Journal of Biological Chemistry, 271(43): 26850–26854 (1996).
Leberer et al., The EMBO Journal, 16(1): 83–97 (1997).
Peter et al., The EMBO Journal, 15(24): 7046–7059 (1996).
Evangelista et al., Science, 276: 118–122 (1997).
Fehon et al., Genetics, 146: 245–252 (1997).
Davis et al., The Journal of Biological Chemistry, 273(2): 849–858 (1998).
Oehlen et al., The Journal of Biological Chemistry, 273(15) 8556–8559 (1998).
Tjandra et al., Current Biology, 8: 991–1000 (1998).
McCraith et al., The Journal of Biological Chemistry, 266(18): 11986–11992 (1991).
McCraith et al., Molecular and Cellular Biology, 10(3): 1049–1055 (1990).
Culver et al., The Journal of Biological Chemistry, 272(20): 13203–13210 (1997).
Spinelli et al., RNA, 3: 1388–1400 (1997).
Spinelli et al., The Journal of Biological Chemistry, 274(5): 2637–2644 (1999).
Spinelli et al., Proc. Natl. Acad. Sci. USA, 95: 14136–14141 (1998).
Jonniaux et al., Yeast, 10: 1639–1645 (1994).
Mosch et al., Genetics, 145: 671–684 (1997).

FUNGAL TARGET GENES AND METHODS

FIELD OF THE INVENTION

The invention relates to genes isolated from *Ashbya gossypii* that encode proteins essential for fungal growth and development. The invention also includes the methods of using these proteins as fungal targets, based on the essentiality of these genes for normal fungal growth and development. The invention is also useful as a screening assay to identify inhibitors that are potential fungicides.

BACKGROUND OF THE INVENTION

The phytopathogenic fungus *Ashbya gossypii* is a filamentously growing ascomycete that was first isolated as a plant pathogen in tropical and sub-tropical regions. It infects the seed capsule of cotton plants (Ashby S. F. and Nowell W. (1926) Ann. Botany 40: 69–84) and has also been isolated from tomatoes and citrus fruits (Phaff H. J. and Starmer W. T. (1987) In "The Yeasts", Vol. I Rose A. H., Harrison, J. S. (eds), Academic Press, London, 123 ff; Dammer K. H. and Ravelo H. G. (1990). Arch. Phytopathol. Pflanzenschutz, Berlin 26: 71–78 Dammer and Ravelo, 1990). The infection of the seed capsule is caused by transmission of *A. gossyppii* mycelium pieces or spores by stinging-sucking insects and causes a disease called stigmatomycosis.

Studies characterising the karyotype of *A. gossypii* have been performed (Wright, 1990; Wendland, 1993; Gaudenz, 1994, "The small genome of the filamentous fungus *Ashbya gossypii*: Assessment of the karyotype", Diploma Thesis, Department of Applied Microbiology, Biocenter, University Basel). It has been found using yeast chromosomes of precisely known length as size markers that the genome of *A. gossypii* has a total nuclear genome size of 8.85 Mb. Presently, *A. gossypii* represents the most compact eukaryotic genome, compared to genome sizes of 12.5 Mb for *Saccharomyces cerevisiae* (Chu et al. (1986) Science, 234:1582–1585), 31.0 Mb for *Aspergillus nidulans* (Brody and Carbon (1989) Proc Natl Acad Sci USA. 86:6260–6263), and 47.0 Mb for *Neurospora crassa* (Orbach et al.(1988) Mol Cell Biology, 8:1469–1473).

*A. gossypii* is systematically grouped to the endomycetales belonging to the family of spermophthoraceae. This classification is based on the observation that the spores that develop in hyphal compartments called sporangia look like ascospores, which are defined as end products of meiosis.

Since *A. gossypii* is a filamentous ascomycete, and is capable of growing only by filamentous (hyphal) growth, fungal targets found in this model organism are predictive of targets which will be found in other pathogens, the vast majority of which grow in a filamentous fashion.

SUMMARY OF THE INVENTION

It is an object of the invention to provide an effective and beneficial method to identify novel fungicides. A feature of the invention is the identification of genes in A. gossypii having a putative biological activity based on their similarity to yeast genes. Genes of the invention comprise a putative MAP kinase kinase class, MKK2 and MKK1 gene (herein referred to as AG012gene), a putative squalene synthetase, ERG9 gene (AG013), a putative mannosyl transferase, OCH1 gene (AG014), a putative RNA 3'-terminal phosphate cyclase, YOL010w gene (AG015), a putative zinc-finger-containing transcriptional repressor, MOT2 gene (AG016), a putative IPC synthase, AUR1 gene (AG017), a putative calcium binding protein, CDC24 gene (AG018), a homologue of RHO subfamily members of RAS-like proteins, CDC42 gene (AG019), a putative tRNA 2'-phosphotransferase, TPT1 gene (AG020), and a putative RNA binding protein, WHI3 gene (AG021). Another feature of the invention is the discovery that the genes of the invention, AG012 (SEQ ID NO:1), AG013 (SEQ ID NO:3), AG014 (SEQ ID NO:5), AG015 (SEQ ID NO:7), AG016 (SEQ ID NO:9), AG017 (SEQ ID NO:11), AG018 (SEQ ID NO:13), AG019 (SEQ ID NO:15), AG020 (SEQ ID NO:17), and AG021 (SEQ ID NO:19) are essential for fungal growth and development. An advantage of the present invention is that the newly discovered essential genes provide the basis for identity of a novel fungicidal mode of action which enables one skilled in the art to easily and rapidly discover novel inhibitors of gene function useful as fungicides.

One object of the present invention is to provide an essential gene in fungi for assay development for inhibitory compounds with fungicidal activity. Genetic results show that when any of the genes described above are mutated in *A. gossypii*, the resulting phenotype ranges from suppressed growth to lethality. Suppressed growth as used herein results in a growth rate of half the growth rate observed in wild-type, or lower, e.g. 10% to 50% of the wild-type growth rate is observed, or no growth is detected at all macroscopically. Furthermore, when some of the genes described above are mutated in *A. gossypii*, abnormal filament development is observed. This demonstrates a critical role for the gene products encoded by these genes.

Using PCR-based gene disruption, the inventors of the present invention have demonstrated that the activities of these gene products are essential for *A. gossypii* growth. Thus, chemicals which inhibit the function of any of these gene products in fungi are likely to have detrimental effects on fungi, and are potentially good fungicide candidates. The present invention therefore provides methods of using a purified protein encoded by either the AG012, AG013, AG014, AG015, AG016, AG017, AG018, AG019, AG020, or AG021 gene, described below to identify inhibitors thereof, which can then be used as fungicides to suppress the growth of pathogenic fungi. Pathogenic fungi are defined as those capable of colonizing a host and causing disease. Examples of fungal pathogens include plant pathogens such as *Septoria tritici, Stagnospora nodorum, Botrytis cinerea, Fusarium graminearum, Magnaporthe grisea, Cochliobolus heterostrophus, Colletotrichum heterostrophus, Ustilago maydis, Erisyphe graminis*, plant pathogenic oomycetes such as *Pythium ultimum* and *Phytophthora infestans*, and human pathogens such as *Candida albicans* and *Aspergillus fumigatus*.

The present invention discloses novel nucleotide sequences derived from *A.gossypii*, designated the AG012, AG013, AG014, AG015, AG016, AG017, AG018, AG019, AG020, and AG021 genes. The nucleotide sequence of the ORF in the genomic clones is set forth in SEQ ID NO:1 (AG012), SEQ ID NO:3 (AG013), SEQ ID NO:5 (AG014), SEQ ID NO:7 (AG015), SEQ ID NO:9 (AG016), SEQ ID NO:11 (AG017), SEQ ID NO:13 (AG018), SEQ ID NO:15 (AG019), SEQ ID NO:17 (AG020), and SEQ ID NO:19 (AG021). The amino acid sequences encoded by the above sequences are set forth in SEQ ID NO:2 (AG012), SEQ ID NO:4 (AG013), SEQ ID NO:6 (AG014), SEQ ID NO:8 (AG015), SEQ ID NO:10 (AG016), SEQ ID NO:12 (AG017),SEQ ID NO:14(AG018),SEQ ID NO:16(AG019), SEQ ID NO:18(AG020), and SEQ ID NO:20 (AG021), respectively. The present invention also includes nucleotide sequences substantially similar to those set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19. The present invention also encompasses fungal proteins whose amino acid sequence are substantially similar to the amino acid sequences set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20. The present invention also includes methods of using these gene products as fungal targets, based on the essentiality of the genes for normal fungal growth and development. Furthermore, the invention can be used in a screening assay to identify inhibitors of AG012, AG013, AG014, AG015, AG016, AG017, AG018, AG019, AG020, or AG021 gene function that are potential fungicides.

Other objects and advantages of the present invention will become apparent to those skilled in the art from a study of the following description of the invention and non-limiting examples.

DEFINITIONS

For clarity, certain terms used in the specification are defined and presented as follows:

Cofactor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

DNA shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme activity: means herein the ability of an enzyme to catalyze the conversion of a substrate into a product. A substrate for the enzyme comprises the natural substrate of the enzyme but also comprises analogues of the natural substrate which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Fungicide: a chemical substance used to kill or suppress the growth of fungal cells.

Heterologous DNA Sequence: a DNA sequence not naturally associated with a host cell into which it is introduced, including non-naturally occurring multiple copies of a naturally occurring DNA sequence; and genetic constructs wherein an otherwise homologous DNA sequence is operatively linked to a non-native sequence.

Homologous DNA Sequence: a DNA sequence naturally associated with a host cell into which it is introduced.

Inhibitor: a chemical substance that causes abnormal growth, e.g., by inactivating the enzymatic activity of a protein such as a biosynthetic enzyme, receptor, signal transduction protein, structural gene product, or transport protein that is essential to the growth or survival of the fungus. In the context of the instant invention, an inhibitor is a chemical substance that alters the enzymatic activity encoded by the AG012, AG013, AG014, AG015, AG016, AG017, AG018, AG019, AG020, or AG021 genes from a fungus. More generally, an inhibitor causes abnormal growth of a host cell by interacting with the gene product encoded by the AG012, AG013, AG014, AG015, AG016, AG017, AG018, AG019, AG020, or AG021 genes.

Isogenic: fungi which are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a fungus (i.e. enzyme activity that occurs naturally in the absence of direct or indirect manipulation of such activity by man), which is tolerant to inhibitors that inhibit the naturally occurring enzyme activity.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

In its bro adest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably 80%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0. The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1X SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "AG012, AG013, AG014, AG015, AG016, AG017, AG018, AG019, AG020, or AG021 gene" refers to a DNA molecule comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 or comprising a nucleotide sequence substantially similar to SEQ ID NO:1, SEQ ID NO:3, SEQ ID NO:5, SEQ ID NO:7, SEQ ID NO:9, SEQ ID NO:11, SEQ ID NO: 13, SEQ ID NO: 15, SEQ ID NO: 17, or SEQ ID NO: 19. Homologs of these genes include nucleotide sequences that encode an amino acid sequence that is at least 25% identical, preferably 40% identical to SEQ ID NO:2, SEQ ID NO:4, SEQ ID NO:6, SEQ ID NO:8, SEQ ID NO:10, SEQ ID NO:10, SEQ ID NO:12, SEQ ID NO:14, SEQ ID NO:16, SEQ ID NO:18, or SEQ ID NO:20 as measured, using the parameters described below, wherein the amino acid sequence encoded by the homolog has the biological activity of the AG012, AG013, AG014, AG015, AG016, AG017, AG018, AG019, AG020, or AG021 protein.

The term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 80%, preferably at least 85%, more preferably at least 90%, still more preferably at least 95%, yet still more preferably at least 99%, using default BLAST analysis parameters BLAST 2.0.7. As used herein the term "AG012, AG013, AG014, AG015, AG016, AG017, AG018, AG019, AG020, or AG021 protein" refers to an amino acid sequence encoded by a DNA molecule comprising a nucleotide sequence substantially similar to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. Homologs of the AG012, AG013, AG014, AG015, AG016, AG017, AG018, AG019, AG020, or AG021 proteins are amino acid sequences that are at least 25% identical, preferably 45% identical, to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 as measured using the parameters described above, wherein the amino acid sequence encoded by the homolog has the biological activity of the AG012, AG013, AG014, AG015, AG016, AG017, AG018, AG019, AG020, or AG021 protein.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Tolerance: the ability to continue essentially normal growth or function when exposed to an inhibitor or fungicide in an amount sufficient to suppress the normal growth or function of native, unmodified fungi.

Transformation: a process for introducing heterologous DNA into a cell, tissue, or fungus. Transformed cells, tissues, or fungi are understood to encompass not only the end product of a transformation process, but also transgenic progeny thereof.

Transgenic: stably transformed with a recombinant DNA molecule that preferably comprises a suitable promoter operatively linked to a DNA sequence of interest.

BRIEF DESCRIPTION OF THE SEQUENCES IN THE SEQUENCE LISTING

SEQ ID NO:1 Genomic DNA coding sequence for the *Ashbya gossypii* AG012 gene

SEQ ID NO:2 Amino acid sequence encoded by the *Ashbya gossypii* AG012 DNA sequence shown in SEQ ID NO:1

SEQ ID NO:3 Genomic DNA coding sequence for the *Ashbya gossypii* AG013 gene

SEQ ID NO:4 Amino acid sequence encoded by the *Ashbya gossypii* AG013 DNA sequence shown in SEQ ID NO:3

SEQ ID NO:5 Genomic DNA coding sequence for the *Ashbya gossypii* AG014 gene

SEQ ID NO:6 Amino acid sequence encoded by the *Ashbya gossypii* AG014 DNA sequence shown in SEQ ID NO:5

SEQ ID NO:7 Genomic DNA coding sequence for the *Ashbya gossypii* AG015 gene

SEQ ID NO:8 Amino acid sequence encoded by the *Ashbya gossypii* AG015 DNA sequence shown in SEQ ID NO:7

SEQ ID NO:9 Genomic DNA coding sequence for the *Ashbya gossypii* AG016 gene

SEQ ID NO:10 Amino acid sequence encoded by the *Ashbya gossypii* AG016 DNA sequence shown in SEQ ID NO:9

SEQ ID NO:11 Genomic DNA coding sequence for the *Ashbya gossypii* AG017 gene

SEQ ID NO:12 Amino acid sequence encoded by the *Ashbya gossypii* AG017 DNA sequence shown in SEQ ID NO:11

SEQ ID NO:13 Genomic DNA coding sequence for the *Ashbya gossypii* AG018 gene

SEQ ID NO:14 Amino acid sequence encoded by the *Ashbya gossypii* AG018 DNA sequence shown in SEQ ID NO:13

SEQ ID NO:15 Genomic DNA coding sequence for the *Ashbya gossypii* AG019 gene

SEQ ID NO:16 Amino acid sequence encoded by the *Ashbya gossypii* AG019 DNA sequence shown in SEQ ID NO:15

SEQ ID NO:17 Genomic DNA coding sequence for the *Ashbya gossypii* AG020 gene

SEQ ID NO:18 Amino acid sequence encoded by the *Ashbya gossypii* AG020 DNA sequence shown in SEQ ID NO:17

SEQ ID NO:19 Genomic DNA coding sequence for the *Ashbya gossypii* AG021 gene

SEQ ID NO:20 Amino acid sequence encoded by the *Ashbya gossypii* AG021 DNA sequence shown in SEQ ID NO:19

SEQ ID NO:21 oligonucleotide primer S1

SEQ ID NO:22 oligonucleotide primer S2

SEQ ID NO:23 oligonucleotide primer G2

SEQ ID NO:24 oligonucleotide primer G3

SEQ ID NO:25 oligonucleotide primer AG012, S1

SEQ ID NO:26 oligonucleotide primer AG012, S2

SEQ ID NO:27 oligonucleotide primer AG013, S1

SEQ ID NO:28 oligonucleotide primer AG013, S2

SEQ ID NO:29 oligonucleotide primer AG014, S1

SEQ ID NO:30 oligonucleotide primer AG014, S2

SEQ ID NO:31 oligonucleotide primer AG015, S1

SEQ ID NO:32 oligonucleotide primer AG015, S2

SEQ ID NO:33 oligonucleotide primer AG016, S1

SEQ ID NO:34 oligonucleotide primer AG016, S2

SEQ ID NO:35 oligonucleotide primer AG017, S1

SEQ ID NO:36 oligonucleotide primer AG017, S2

SEQ ID NO:37 oligonucleotide primer AG018, S1

SEQ ID NO:38 oligonucleotide primer AG018, S2

SEQ ID NO:39 oligonucleotide primer AG019, S1

SEQ ID NO:40 oligonucleotide primer AG019, S2

SEQ ID NO:41 oligonucleotide primer AG020, S1

SEQ ID NO:42 oligonucleotide primer AG020, S2

SEQ ID NO:43 oligonucleotide primer AG021, S1

SEQ ID NO:44 oligonucleotide primer AG021, S2

DETAILED DESCRIPTION OF THE INVENTION

In a preferred embodiment, the proteins having AG012, AG013, AG014, AG015, AG016, AG017, AG018, AG019, AG020, and AG021 activities are encoded by nucleotide sequences derived from fungi, preferably filamentous fungi, particularly from *Ashbya gossypii*, desirably identical or substantially similar to the nucleotide sequences set forth in SEQ ID NO:1, SEQ ID NO:3, SEQ ID NO:5, SEQ ID NO: 7, SEQ ID NO:9, SEQ ID NO:11, SEQ ID NO:13, SEQ ID NO:15, SEQ ID NO:17, or SEQ ID NO:19. In another embodiment, the proteins having AG012, AG013, AG014, AG015, AG016, AG017, AG018, AG019, AG020, and AG021 activities are encoded by nucleotide sequences capable of encoding the amino acid sequences of SEQ ID NO:2, SEQ ID NO:4, SEQ ID NO:6, SEQ ID NO:8, SEQ ID NO:10, SEQ ID NO:10, SEQ ID NO:12, SEQ ID NO:14, SEQ ID NO:16, SEQ ID NO:18, or SEQ ID NO:20. In yet another embodiment, the proteins having AG012, AG013, AG014, AG015, AG016, AG017, AG018, AG019, AG020, and AG021 activities have amino acid sequences identical or substantially similar to the amino acid sequences set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, respectively.

In a preferred embodiment, the present invention describes a method for identifying chemicals having the ability to inhibit any one or more of AG012, AG013, AG014, AG015, AG016, AG017, AG018, AG019, AG020, or AG021 activity in fungi preferably comprising the steps of: a) obtaining transgenic fungus and/or fungal cell, preferably stably transformed, comprising a non-native nuclcotide sequence or an endogenous nucleotide sequence operably linked to non-native promoter, preferably an inducible promoter, encoding an enzyme having an activity and capable of overexpressing an enzymatically active AG012, AG013, AG014, AG015, AG016, AG017, AG018, AG019, AG020, or AG021 gene product where overexpression of the gene product suppresses or inhibits the normal growth and development of the fungus; b) applying a compound to the transgenic fungus and/or fungal cell c) determining the growth and/or development of the transgenic fungus and/or fungal cell after application of the compound; d) comparing the growth and/or development of the transgenic fungus and/or fungal cell after application of the chemical to the growth and/or development of the corresponding transgenic fungus and/or fungal cell to which the compound was not applied; and e) selecting a compound that does result in reduction of the suppressed or inhibited growth and/or development in the transgenic fungus and/or fungal cell in comparison to the untreated transgenic fungus and/or fungal cell.

The invention also provides a method for suppressing the growth of a fungus comprising the step of applying to the fungus a compound that inhibits the naturally occurring AG012, AG013, AG014, AG015, AG016, AG017, AG018, AG019, AG020, and/or AG021 activity in the fungus. Normal growth is defined as a growth rate substantially similar to that observed in wild type fungus, preferably greater than at least 50% the growth rate observed in wild type fungus and particularly greater than 10% the growth rate observed in wild type fungus. Normal growth and development may also be defined, when used in relation to filamentous fungi, as normal filament development (including normal septation, normal nuclear migration and distribution), normal sporulation, and normal production of any infection structures (e.g. appressoria). Conversely, suppressed or inhibited growth as used herein is defined as less than half the growth rate observed in wild type or lower where 10% that of the wild-type growth rate is observed or no growth is macroscopically detected at all or abnormal filament development.

In a further embodiment according to the invention, a DNA sequence selected from the Sequence Listing may also be used for distinguishing among different species of plant pathogenic fungi and for distinguishing fungal pathogens from other pathogens such as bacteria.

I. Essentiality of the AG012, AG013, AG014, AG015, AG016, AG017, AG018, AG019, AG020, and AG021 Genes in *Ashbya gossypii* Demonstrated by Gene Disruption As shown in the examples below, the identification of a novel gene structure, as well as the essentiality of the AG012, AG013, AG014, AG015, AG016, AG017, AG018, AG019, AG020, and AG021 genes for normal fungal growth and development, have been demonstrated for the first time in *A. gossypii* using gene disruption. Having established the essentiality of AG012, AG013, AG014, AG015, AG016, AG017, AG018, AG019, AG020, and AG021 function in fungi and having identified the genes encoding these essential activities, the inventors thereby provide an important and sought after tool for new fungicide development.

II. Sequence of the *Ashbya gossypii* Genes

The present invention discloses the genomic nucleotide sequence of the *A. gossypii* AG012, AG013, AG014, AG015, AG016, AG017, AG018, AG019, AG020, and AG021 genes as well as the amino acid sequences of the *A. gossypii* AG012, AG013, AG014, AG015, AG016, AG017, AG018, AG019, AG020, and AG021 proteins. The nucleotide sequence corresponding to the genomic DNA coding region is set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19 and the amino acid sequence encoding the protein is set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20, respectively. The present invention also encompasses an isolated amino acid sequence derived from a fungus, wherein said amino acid sequence is identical or substantially similar to the amino acid sequence encoded by the nucleotide sequence set forth in SEQ ID NO:1, SEQ ID NO:3, SEQ ID NO:5, SEQ ID NO:7, SEQ ID NO:9 SEQ ID NO:11, SEQ ID NO:13, SEQ ID NO:15, SEQ ID NO:17, or SEQ ID NO:19, wherein said amino acid sequence has AG012, AG013, AG014, AG015, AG016, AG017, AG018, AG019, AG020, or AG021 activity. Using BLASTX (2.0.7) programs with the default settings, notable sequence similarities are summarized below.

| Reference Amino Acid Sequence (name, total # amino acid residues) | Genbank Accession # | % Amino Acid Identity |
| --- | --- | --- |
| AG012, 524 amino acids | AAB68220[1] | ~52% from residues 1–522 |
| AG013, 441 amino acids | AAB68360[2] | ~66% from residues 1–438 |
| AG014, 472 amino acids | CAA96740[3] | ~49% from residues 27–456 |
| AG015, 362 amino acids | CAA99009[4] | ~78% from residues 4–362 |
| AG016, 646 amino acids | AAB64604[5] | ~52% from residues 1–514 |
| AG017, 422 amino acids | CAA81836[6] | ~64% from residues 1–400 |
| AG018, 761 amino acids | AAC04990[7] | ~58% from residues 16–757 |
| AG019, 191 amino acids | AAB67416[8] | ~93% from residues 1–191 |
| AG020, 230 amino acids | CAA99116[9] | ~47% from residues 8–227 |
| AG021, 729 amino acids | CAA96092[10] | ~67% from residues 567–706 |
| AG021, 729 amino acids | CAA96092[11] | ~44% from residues 106–386 |

[1]*Saccharomyces cerevisiae* MKK2 gene
[2]*S. cerevisiae* ERG9 gene
[3]*S. cerevisiae* OCH1 gene
[4]*S. cerevisiae* YOL010w gene
[5]*S. cerevisiae* MOT2 gene
[6]*S. cerevisiae* AUR1 gene
[7]*S. cerevisiae* CDC24 gene
[8]*S. cerevisiae* CDC42 gene
[9]*S. cerevisiae* TPT1 gene
[10]*S. cerevisiae* WH13 gene III. Recombinant Production of AG012, AG013, AG014, AG015, AG016, AG017, AG018, AG019, AG020, or AG021 Activity and Uses Thereof For recombinant production of AG012, AG013, AG014, AG015, AG016, AG017, AG018, AG019, AG020, or AG021 activity in a host organism, a nucleotide sequence encoding a protein having AG012, AG013, AG014, AG015, AG016, AG017, AG018, AG019, AG020, or AG021 activity is inserted into an expression cassette designed for the chosen host and introduced into the host where it is recombinantly produced. For example, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, or nucleotide sequences substantially similar to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, or homologs of the AG012, AG013, AG014, AG015, AG016, AG017, AG018, AG019, AG020, or AG021 coding sequence can be used for the recombinant production of a protein having AG012, AG013, AG014, AG015, AG016, AG017, AG018, AG019, AG020, or AG021 activity. The choice of specific regulatory sequences such as promoter, signal sequence, 5' and 3' untranslated sequences, and enhancer appropriate for the chosen host is within the level of skill of the routineer in the art. The resultant molecule, containing the individual elements operably linked in proper reading frame, may be inserted into a vector capable of being transformed into the host cell. Suitable expression vectors and methods for recombinant production of proteins are well known for host organisms such as *E. coli*, yeast, and insect cells (see, e.g., Luckow and Summers, *Bio/Technol.* 6: 47 (1988), and baculovirus expression vectors, e.g., those derived from the genome of *Autographica californica* nuclear polyhedrosis virus (AcMNPV). A preferred baculovirus/insect system is pAcHLT (Pharmingen, San Diego, Calif.) used to transfect *Spodoptera frugiperda* Sf9 cells (ATCC) in the presence of linear *Autographa californica* baculovirus DNA (Pharmigen, San Diego, Calif.). The resulting virus is used to infect HighFive *Tricoplusia ni* cells (Invitrogen, La Jolla, Calif.).

In a preferred embodiment, the nucleotide sequence encoding a protein having AG012, AG013, AG014, AG015, AG016, AG017, AG018, AG019, AG020, or AG021 activity is derived from an eukaryote, such as a mammal, a fly or a yeast, but is preferably derived from a fungus. In a further preferred embodiment, the nucleotide sequence is identical or substantially similar to the nuclcotide sequence set forth in SEQ ID NO:1, SEQ ID NO:3, SEQ ID NO:5, SEQ ID NO:7, or SEQ ID NO:9, SEQ ID NO:11, SEQ ID NO:13, SEQ ID NO:15, SEQ ID NO:17, or SEQ ID NO:19, encodes a protein having AG012, AG013, AG014, AG015, AG016, AG017, AG018, AG019, AG020, or AG021 activity, whose amino acid sequence is identical or substantially similar to the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. The nucleotide sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, encodes the *A. gossypii* protein, whose amino acid sequence is set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. In another preferred embodiment, the nucleotide sequence is derived from a prokaryote, preferably a bacteria, e.g. *E. coli*. Recombinantly produced protein having AG012, AG013, AG014, AG015, AG016, AG017, AG018, AG019, AG020, or AG021 activity is isolated and purified using a variety of standard techniques. The actual techniques that may be used will vary depending upon the host organism used, whether the protein is designed for secretion, and other such factors familiar to the skilled artisan (see, e.g. chapter 16 of Ausubel, F. et al., "Current Protocols in Molecular Biology", pub. by John Wiley & Sons, Inc. (1994).

IV. Assays for Characterizing the AG012, AG013, AG014, AG015, AG016, AG017, AG018, AG019, AG020, and AG021 Proteins Recombinantly produced AG012, AG013, AG014, AG015, AG016, AG017, AG018, AG019, AG020, and AG021 proteins are useful for a variety of purposes. For example, they can be used in in vitro assays to screen for known fungicidal chemicals, whose target has not been identified, to determine if they inhibit AG012, AG013, AG014, AG015, AG016, AG017, AG018, AG019, AG020, or AG021 . Such in vitro assays may also be used as more general screens to identify chemicals that inhibit such enzymatic activities and that are therefore novel fungicide candidates. Alternatively, recombinantly produced AG012, AG013, AG014, AG015, AG016, AG017, AG018, AG019, AG020, or AG021 proteins are used to elucidate the complex structure of these molecules and to further characterize their association with known inhibitors in order to rationally design new inhibitory fungicides. Nucleotide sequences substantially similar to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, and proteins substantially similar to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20, from any source, including microbial sources, can be used in the assays exemplified herein. Desirably such nucleotide sequences and proteins are derived from fungi. More desirably, they are derived from filamentous fungi, particularly *Ashbya gossypii*. Alternatively, such nucleotide sequences and proteins are derived from non-yeast sources, alternatively from non-*Saccharomyces cerevisiae* sources.

A simple assay is developed to screen for compounds that affect normal functioning of the fungal-encoded activity. Such compounds are promising in vitro leads that can be tested for in vivo fungicidal activity. A nucleic acid sequence of the invention according to any one of the sequences SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, is operably linked to a strong inducible promoter, such promoters being known in the art. The vector comprising the selected gene of the invention operably linked to the selected inducible promoter is transformed into bacteria, such as *E. coli*. Transformed *E. coli* harboring and functionally overexpressing an AG012, AG013, AG014, AG015, AG016, AG017, AG018, AG019, AG020, or AG021 gene are grown in a 96-well format for automated high-throughput screening where inducible over expression of the selected gene is lethal or suppresses growth of the host. Compounds that are effective in blocking function of the AG012, AG013, AG014, AG015, AG016, AG017, AG018, AG019, AG020, or AG021 protein result in bacterial growth. This growth is measured by simple turbidometric means.

In another embodiment, an assay for inhibitors of the AG012, AG013, AG014, AG015, AG016, AG017, AG018, AG019, AG020, or AG021 activities uses transgenic fungi or fungal cells capable of overexpressing a nucleotide sequence having AG012, AG013, AG014, AG015, AG016, AG017, AG018, AG019, AG020, or AG021 activity, respectively, operably linked to a strong inducible promoter, e.g., wherein the selected gene product is enzymatically active in the transgenic fungi and/or fungal cells, and inducible overexpression of the gene inhibits and/or suppresses growth and/or development of the fungus. The nucleotide sequence is preferably derived from an eukaryote, such as a yeast, but is preferably derived from a fungus and more particularly from a filamentous fungus. In a further preferred embodiment, the nucleic acid sequences set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. SEQ ID NO:1, SEQ ID NO:3, SEQ ID NO:5, SEQ ID NO:7, SEQ IDNO:9, SEQ ID NO:11, SEQ ID NO:13, SEQ ID NO:15, SEQ ID NO:17, or SEQ ID NO:19 encode enzymes having AG012, AG013, AG014, AG015, AG016, AG017, AG018, AG019, AG020, or AG021 respectively, whose amino acid sequence is identical or substantially similar to the amino acid sequence set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. The transgenic fungus or fungal cells are grown in 96-well format microtiter dishes for high-throughput screening. Compounds that are effective in blocking function of the AG012, AG013, AG014, AG015, AG016, AG017, AG018, AG019, AG020, or AG021 protein results in fungal growth. This growth is measured by methods known in the art. In a particular embodiment, the transgenic fungus is *Ashbya gossypii*.

Similar assays, based on expression of the fungal genes of the invention in yeast, using appropriate expression systems, as described above, may also be used.

In Vitro Inhibitor Assays: Discovery of Small Molecule Ligand that Interacts with the Gene Product of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19

Once a protein has been identified as a potential fungicide target, the next step is to develop an assay that allows screening large number of chemicals to determine which ones interact with the protein. Although it is straightforward to develop assays for proteins of known function, developing assays with proteins of unknown functions is more difficult.

This difficulty can be overcome by using technologies that can detect interactions between a protein and a compound without knowing the biological function of the protein. A short description of three methods is presented, including fluorescence correlation spectroscopy, surface-enhanced laser desorption/ionization, and biacore technologies.

Fluorescence Correlation Spectroscopy (FCS) theory was developed in 1972 but it is only in recent years that the technology to perform FCS became available (Madge et al. (1972) Phys. Rev. Lctt., 29: 705–708; Maiti et al. (1997) Proc. Natl. Acad. Sci. USA, 94: 11753–11757). FCS measures the average diffusion rate of a fluorescent molecule within a small sample volume. The sample size can be as low as $10^3$ fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analysed is expressed as a recombinant protein with a sequence tag, such as a poly-histidine sequence, inserted at the N or C-terminus. The expression takes place in either *E. coli*, yeast or insect cells. The protein is purified by chromatography. For example, the poly-histidine tag can be used to bind the expressed protein to a metal chelate column such as Ni2+ chelated on iminodiacetic acid agarose. The protein is then labelled with a fluorescent tag such as carboxytetramethylrhodamine or BODIPY® (Molecular Probes, Eugene, Oreg.). The protein is then exposed in solution to the potential ligand, and its diffusion rate is determined by FCS using instrumentation available from Carl Zeiss, Inc. (Thornwood, N.Y.). Ligand binding is determined by changes in the diffusion rate of the protein.

Surface-Enhanced Laser Desorption/Ionization (SELDI) was invented by Hutchens and Yip during the late 1980's (Hutchens and Yip (1993) Rapid Commun. Mass Spectrom. 7: 576–580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules that bind to this protein (Worrall et al. (1998) Anal. Biochem. 70: 750–756). In a typical experiment, the target to be analysed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system capable to pipet the ligands in a sequential manner (autosampler). The chip is then submitted to washes of increasing stringency, for example a series of washes with buffer solutions containing an increasing ionic strength. After each wash, the bound material is analysed by submitting the chip to SELDI-TOF. Ligands that specifically bind the target will be identified by the stringency of the wash needed to elute them.

Biacore relies on changes in the refractive index at the surface layer upon binding of a ligand to a protein immobilized on the layer. In this system, a collection of small ligands is injected sequentially in a 2–5 ul cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299–304; Malmquist (1993) Nature, 361: 186–187). In a typical experiment, the target to be analysed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

V. In Vivo Inhibitor Assay

In one embodiment, a suspected fungicide, for example identified by in vitro screening, is applied to fungi at various concentrations. After application of the suspected fungicide, its effect on the fungus, for example inhibition or suppression of growth and development is recorded.

VI. Generating Derivatives of AG012, AG013, AG014, AG015, AG016, AG17, AG018, AG019, AG020, or AG021 Proteins Fungicide resistant AG012, AG013, AG014, AG015, AG016, AG017, AG018, AG019, AG020, or AG021 proteins are also obtained using methods involving in vitro recombination, also called DNA shuffling. By DNA shuffling, mutations, preferably random mutations, are introduced into nucleotide sequences encoding AG012, AG013, AG014, AG015, AG016, AG017, AG018, AG019, AG020, or AG021 activity. DNA shuffling also leads to the recombination and rearrangement of sequences within a AG012, AG013, AG014, AG015, AG016, AG017, AG018, AG019, AG020, or AG021 gene or to recombination and exchange of sequences between two or more different of AG012, AG013, AG014, AG015, AG016, AG017, AG018, AG019, AG020, or AG021 genes. These methods allow for the production of millions of mutated AG012, AG013, AG014, AG015, AG016, AG017, AG018, AG019, AG020, or AG021 coding sequences. The mutated genes, or shuffled genes, are screened for desirable properties, e.g. improved tolerance to fungicides and for mutations that provide broad spectrum tolerance to the different classes of inhibitor chemistry. Such screens are well within the skills of a routineer in the art.

In a preferred embodiment, a mutagenized AG012, AG013, AG014, AG015, AG016, AG017, AG018, AG019, AG020, or AG021 gene is formed from at least one template AG012, AG013, AG014, AG015, AG016, AG017, AG018, AG019, AG020, or AG021 gene, wherein the template AG012, AG013, AG014, AG015, AG016, AG017, AG018, AG019, AG020, or AG021 gene has been cleaved into double-stranded random fragments of a desired size, , and comprising the steps of adding to the resultant population of double-stranded random fragments one or more single or double-stranded oligonucleotides, wherein said oligonucleotides comprise an area of identity and an area of heterology to the double-stranded random fragments; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide, wherein the mutagenized polynucleotide is a mutated AG012, AG013, AG014, AG015, AG016, AG017, AG018, AG019, AG020, or AG021 gene having enhanced tolerance to a fungicide which inhibits naturally occurring AG012, AG013, AG014, AG015, AG016, AG017, AG018, AG019, AG020, or AG021 activity. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles. Such method is described e.g. in Stemmer et al. (1994) Nature 370: 389–391, in U.S. Pat. No. 5,605,793, U.S. Pat. No. 5,811,238 and in Cramcri et al. (1998) Nature 391: 288–291, as well as in WO 97/20078, and these references are incorporated herein by reference.

In another preferred embodiment, any combination of two or more different AG012, AG013, AG014, AG015, AG016, AG017, AG018, AG019, AG020, or AG021 genes are mutagenized in vitro by a staggered extension process (StEP), as described e.g. in Zhao et al. (1998) Nature Biotechnology 16: 258–261. The two or more AG012, AG013, AG014, AG015, AG016, AG017, AG018, AG019, AG020, or AG021 genes are used as template for PCR amplification with the extension cycles of the PCR reaction preferably carried out at a lower temperature than the optimal polymerization temperature of the polymerase. For example, when a thermostable polymerase with an optimal temperature of approximately 72° C. is used, the temperature for the extension reaction is desirably below 72° C., more desirably below 65° C., preferably below 60° C., more preferably the temperature for the extension reaction is 55° C. Additionally, the duration of the extension reaction of the PCR cycles is desirably shorter than usually carried out in the art, more desirably it is less than 30 seconds, preferably it is less than 15 seconds, more preferably the duration of the extension reaction is 5 seconds. Only a short DNA fragment is polymerized in each extension reaction, allowing template switch of the extension products between the starting DNA molecules after each cycle of denaturation and annealing, thereby generating diversity among the extension products. The optimal number of cycles in the PCR reaction depends on the length of the AG012, AG013, AG014, AG015, AG016, AG017, AG018, AG019, AG020, or AG021 genes to be mutagenized but desirably over 40 cycles, more desirably over 60 cycles, preferably over 80 cycles are used. Optimal extension conditions and the optimal number of PCR cycles for every combination of AG012, AG013, AG014, AG015, AG016, AG017, AG018, AG019, AG020, or AG021 genes are determined as described in using procedures well-known in the art. The other parameters for the PCR reaction are essentially the same as commonly used in the art. The primers for the amplification reaction are preferably designed to anneal to DNA sequences located outside of the AG012, AG013, AG014, AG015, AG016, AG017, AG018, AG019, AG020, or AG021 genes, e.g. to DNA sequences of a vector comprising the AG012, AG013, AG014, AG015, AG016, AG017, AG018, AG019, AG020, or AG021 genes, whereby the different AG012, AG013, AG014, AG015, AG016, AG017, AG018, AG019, AG020, or AG021 genes used in the PCR reaction are preferably comprised in separate vectors. The primers desirably anneal to sequences located less than 500 bp away from AG012, AG013, AG014, AG015, AG016, AG017, AG018, AG019, AG020, or AG021 sequences, preferably less than 200 bp away from the AG012, AG013, AG014, AG015, AG016, AG017, AG018, AG019, AG020, or AG021 sequences, more preferably less than 120 bp away from the AG012, AG013, AG014, AG015 AG016, AG017, AG018, AG019, AG020, or AG021 sequences. Preferably, the AG012, AG013, AG014, AG015, AG016, AG017, AG018, AG019, AG020, or AG021 sequences are surrounded by restriction sites, which are included in the DNA sequence amplified during the PCR reaction, thereby facilitating the cloning of the amplified products into a suitable vector. In another preferred embodiment, fragments of AG012, AG013, AG014, AG015, AG016, AG017, AG018, AG019, AG020, or AG021 genes having cohesive ends are produced as described in WO 98/05765. The cohesive ends are produced by ligating a first oligonucleotide corresponding to a part of a AG012, AG013, AG014, AG015, AG016, AG017, AG018, AG019, AG020, or AG021 gene to a second oligonucleotide not present in the gene or corresponding to a part of the gene not adjoining to the part of the gene corresponding to the first oligonucleotide, wherein the second oligonucleotide contains at least one ribonucleotide. A double-stranded DNA is produced using the first oligonucleotide as template and the second oligonucleotide as primer. The ribonucleotide is cleaved and removed. The nucleotide(s) located 5' to the ribonucleotide is also removed, resulting in double-stranded fragments having cohesive ends. Such fragments are randomly reassembled by ligation to obtain novel combinations of gene sequences.

Any AG012, AG013, AG014, AG015, AG016, AG017, AG018, AG019, AG020, or AG021 gene or any combination of AG012, AG013, AG014, AG015, AG016, AG017, AG018, AG019, AG020, or AG021genes, or homologs thereof, is used for in vitro recombination in the context of the present invention, for example, a AG012, AG013, AG014, AG015, AG016, AG017, AG018, AG019, AG020, or AG021 gene derived from a fungus, such as, e.g. *Ashbya gossypii*, e.g. a AG012, AG013, AG014, AG015 AG016, AG017, AG018, AG019, AG020, or AG021 gene set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. Whole AG012, AG013, AG014, AG015, AG016, AG017, AG018, AG019, AG020, or AG021 genes or portions thereof are used in the context of the present invention. The library of mutated AG012, AG013, AG014, AG015, AG016, AG017, AG018, AG019, AG020, or AG021 genes obtained by the methods described above are cloned into appropriate expression vectors and the resulting vectors are transformed into an appropriate host, for example a fungal cell, an algae like Chlamydomonas, a yeast or a bacteria. An appropriate host requires AG012, AG013, AG014, AG015, AG016, AG017, AG018, AG019, AG020, or AG021 gene product activity for growth. Host cells transformed with the vectors comprising the library of mutated AG012, AG013, AG014, AG015, AG016, AG017, AG018, AG019, AG020, or AG021 genes are cultured on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

An assay for identifying a modified AG012, AG013, AG014, AG015, AG016, AG017, AG018, AG019, AG020, or AG021 gene that is tolerant to an inhibitor may be performed in the same manner as the assay to identify inhibitors of the AG012, AG013, AG014, AG015, AG016, AG017, AG018, AG019, AG020, or AG021 activity (Inhibitor Assay, above) with the following modifications: First, a mutant AG012, AG013, AG014, AG015, AG016, AG017, AG018, AG019, AG020, or AG021 protein is substituted in one of the reaction mixtures for the wild-type AG012, AG013, AG014, AG015, AG016, AG017, AG018, AG019, AG020, or AG021 protein of the inhibitor assay. Second, an inhibitor of wild-type enzyme is present in both reaction mixtures. Third, mutated activity (activity in the presence of inhibitor and mutated enzyme) and unmutated activity (activity in the presence of inhibitor and wild-type enzyme) are compared to determine whether a significant increase in enzymatic activity is observed in the mutated activity when compared to the unmutated activity. Mutated activity is any measure of activity of the mutated enzyme while in the presence of a suitable substrate and the inhibitor. Unmutated activity is any measure of activity of the wild-type enzyme while in the presence of a suitable substrate and the inhibitor.

VII. Method of Using Genes to Distinguish Fungal Species

In a further embodiment according to the invention, a DNA sequence selected from the Sequence Listing may also be used for distinguishing among different species of plant pathogenic fungi and for distinguishing fungal pathogens from other pathogens such as bacteria (Weising et al. (1995) In "DNA Fingerprinting in Plants and Fungi", CRC Press, Boca Raton, pp. 157–227).

VIII. Fungal Transformation Technology

An AG012, AG013, AG014, AG015, AG016, AG017, AG018, AG019, AG020, or AG021 gene, or homologs thereof, can be incorporated in fungal or bacterial cells using conventional recombinant DNA technology. Generally, this involves inserting a DNA molecule encoding the AG012, AG013, AG014, AG015, AG016, AG017, AG018, AG019, AG020, or AG021 gene into an expression system to which the DNA molecule is heterologous (i.e., not normally present) using standard cloning procedures known in the art. The vector contains the necessary elements for the transcription and translation of the inserted protein-coding sequences in a fungal cell containing the vector. A large number of vector systems known in the art can be used, such as plasmids (van den Hondel and Punt (1990) In "Applied Molecular Genetics of Fungi," Peberdy, Catten, Ogden, Bennett (eds), Cambridge University Press, New York, pp. 1–28). The components of the expression system may also be modified to increase expression. For example, truncated sequences, nucleotide substitutions, nucleotide optimization or other modifications may be employed. Expression systems known in the art can be used to transform fungal cells under suitable conditions (Lemke and Peng (1997) In "The Mycota", Vol. II Kuck (ed), Springer-Verlag, Berlin, pp. 109–139). A heterologous DNA sequence comprising an AG012, AG013, AG014, AG015, AG016, AG017, AG018, AG019, AG020, or AG021 gene is preferably stably transformed and integrated into the genome of the fungal host cells.

Gene sequences intended for expression in transgenic fungi are first assembled in expression cassettes behind a suitable promoter expressible in fungi (Lang-Hinrichs (1997) In "The Mycota", Vol II Kuck (ed), Springer-Verlag, Berlin, pp. 141–153; Jacobs and Stahl (1997) In "The Mycota", Vol II Kuck (ed), Springer-Verlag, Berlin, pp. 155–167). The expression cassettes may also comprise any further sequences required or selected for the expression of the heterologous DNA sequence. Such sequences include, but are not restricted to, transcription terminators, extraneous sequences to enhance expression such as introns, and sequences intended for the targeting of the gene product to specific organelles and cell compartments. These expression cassettes can then be easily transferred to the fungal transformation vectors as described (Lemke and Peng (1997) In "The Mycota", Vol II Kuck (ed), Springer-Verlag, Berlin, pp. 109–139).

EXAMPLES

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Construction and Characterization of a Genomic Library of *A. gossypii* (strain ATCC10895), identification of ORFs and promoters is described in U.S. patent aspplication Ser. No.: 08/998,416 now U.S. Pat. No. 6,239,264, which is hereby incorporated by reference in its entirety.

Example 1

Identification of Antifungal Drug Targets Represented in the Sequence Listing

Gene disruptions of *A. gossypii* genes are generated by a method using short flanking homology regions to produce gene targeting events. The short flanking homology regions are included within polymerase chain reaction primers of 65 nucleotide overall sequence length. Each of these 65-mers contains approximately 45 nucleotides homology to the target gene locus the target gene locus being identified as described in U.S. patent application Ser. No. 08/998,416, now U.S. Pat. No. 6,239,264 incorporated above by reference, and 20 nucleotides homology (invariant) to a geneticin resistance gene module also described in U.S. patent application Ser. No. 08/998,416, now U.S. Pat. No. 6,239,264 previously incorporated by reference), with one primer (designated S1) anchored to the 5' end of the geneticin resistance module (using the invariant sequence 5'-GCTAGGGATAACAGGGTAAT-3') (SEQ ID NO:21) and the other primer of the pair (designated S2) anchored to the 3' end of the geneticin resistance module (using the invariant sequence 5'-AGGCATGCAAGCTTAGATCT-3') (SEQ ID NO:22). The PCR product resulting from the amplification of the geneticin resistance module with such an S1/S2 primer pair thus consists of the module flanked by short flanking homology regions of ca. 45 nucleotides specific to the chosen gene disruption site.

Once an S1/S2 primer pair is designed for a particular gene target, approximately 10 ug of the desired geneticin resistance module is obtained by linearizing a vector containing the geneticin resistance gene positioned behind the an appropriate fungal promoter (for example, the *Saccharoniyces cerevisiae* TEF1 promoter) and subjecting the linearized template to approximately 35 rounds of a PCR reaction consisting of the following steps:

Step 1: Denaturation at 96 C for 30 seconds;
Step 2: Primer annealing at 50 C for 30 seconds;
Step 3: Elongation reaction at 72 C for 2.5 minutes.

Following the 35th round of this protocol, a final elongation period of 5 minutes at 72 C is carried out.

Transformation of the PCR product resulting from amplification with the S1/S2 primer pair is done by electroporation as follows:

1) Inoculate 100 ml of AFM media (1% casein peptone, 2% glucose, 1% yeast extract, 0.1% myo-inositol) with an Ashbya spore suspension of approximately $10^7$ spores.
2) Incubate at 30 C for a maximum of 18 hours at a shaker speed of 200 rpm.
3) Collect the resultant fungal mycelia by filtration and wash once with sterile water.
4) Resuspend 1 gram of mycelia (wet weight) in 40 ml of 50 mM potassium phosphate buffer, pH 7.5 containing 25mM DTT and incubate at 30 C for 30 minutes with gentle shaking.
5) Collect the mycelia by filtration and wash once with 50 ml of cold STM buffer (275 mM sucrose, 10 mM Tris-HCl, pH 7.5, 2 mM $MgCl_2$).
6) Resuspend the mycelia to a dense mixture in STM buffer.
7) Mix approximately 150 ul of the mycelial mixture with 10 ug of PCR product (in a maximum volume of 50 ul) in an Eppendorf tube and transfer the mixture to an electroporation cuvette with a 4 mM gap distance.

8) Apply an electric field pulse of 1.5 kV, 100 ohms, 25 uF which will result in a pulse length of approximately 2.3 milliseconds. Add 1 ml of AFM media to the cuvette and spread equal amounts onto 3 pre-dried AFM agar plates.
9) Incubate plates for a minimum of 4 hours at 30 C.
10) Overlay the plates with 8 ml of a 0.5% agarose toplayer containing Geneticin/G418 at a final concentration of 200 ug/ml.
11) Incubate at 30 C for approximately 3 days to allow sufficient growth of geneticin resistant transformants.

Verification of the desired transformation event resulting in homologous integration of the geneticin resistance module in the target of interest is achieved by PCR using verification primers designated G1 (positioned upstream of the SI region) and G4 (positioned downstream of the S2 region) and template DNA purified from putative Ashbya transformants. Additional verification primers designated G2 (5'-GTTTAGTCTGACCATCTCATCTG-3') (SEQ ID NO:23) and G3 (5'-TCGCAGACCGATACCAGGATC-3') (SEQ ID NO:24) are derived from the open reading frame of the selectable geneticin resistance gene such that the detection of a G1/G2 PCR product and or a G3/G4 PCR product of a predictable size serves to verify the desired gene disruption event. Also, verification of the desired gene disruption can be determined by standard DNA hybridization experiments.

Determination of whether a gene is essential to growth of Ashbya can be achieved by the following analysis. The transformation of DNA fragments described above utilizes multinucleate Ashbya mycelia as recipients. Therefore a primary transformant able to grow on geneticin containing media originates as a mycelium containing cells at least one of which has at least one transformed nucleus, but usually containing non-transformed nuclei as well. Thus, if an essential gene is disrupted in the transformed nucleus, the essential gene product can, in many instances, still be supplied by the non-transformed nuclei within the same cell. Such primary transformants usually exhibit normal growth and sporulation, and spores are collected from primary transformants allowed to grow at 30 C for at least 5 days. Since spores are uninucleate, however, transformants which have an essential gene disrupted in nuclei containing the geneticin resistance cartridge will fail to yield spores which grow normally, if at all, on geneticin-containing media.

S1 and S2 primer pairs usable to generate disruptions of the indicated genes are as follows:
AG012: S1: 5'-GAGGCTGTCAACTCGCTCGCCACT ACGTTTACTGGCACCTCGTACTACATGGCTAGGGAT AACAGGGTAAT-3' (SEQ ID NO:25)
AG012: S2: 5'-GAGACAGTAGCTGATGAATGACTT GAAGGCCTTGCTCCACACGATGTTCGAGGCATG CAAGCTTAGATCT-3' (SEQ ID NO:26)
AG013:S1: 5'-CTCCAACGAGCCCTGCAACATAGTGGC AGTAGCGGTCGTAGTCCTGCTAGGGATAACAGG GTAAT-3' (SEQ ID NO:27)
AG013:S2: 5'-CTTTTGCGGCCGTGATAATGGAGCTAC ATCCCGAGCTGCGCAACGAGGCATGCAAGCTT AGATCT-3' (SEQ ID NO:28)
AG014:S1: 5'-CGTTGGAGGTGCCCAGCTCATACC ACGTCGGGGAGCTGAACATGCGGGAGGCTAGGG ATAACAGGGTAAT-3' (SEQ ID NO:29)
AG014:S2: 5'-CAGGTATCGGAAGAAGTCTGCGCGCA TGATGGCCAGAGGCAGCGACTCAGGCATGCAAG CTTAGATCT- 3' (SEQ ID NO:30)
AG015: S1: 5'-GTCACATTCCGTGGTGCCACGAATTTC CGGCACAGAATAGTGATGGCCACGCTAGGGATAA CAGGGTAAT-3' (SEQ ID NO:31)
AG015: S2: 5'-CTTGATTGTGACGATCAGGTCGTCGGT GTCATCGTCAGCAGGTTTCAGCAGAGGCATGC AAGCTTAGATCT-3' (SEQ ID NO:32)
AG016: S1: 5'-CGGACAGCGTTCAGAGAAGACAGA GACAATCAACACCAAACAAACGCTAGGGATAAC AGGGTAAT-3' (SEQ ID NO:33)
AG016:S2: 5'-AGCAGAACTGACAGATTTGATACC CGCACGGACACGGCTTAAAGTAGGCATGCAAGCTT AGATCT-3' (SEQ ID NO:34)
AG017: S1: 5' CGTTTGTGGTTGCCGCAATACTCTTTA TCTTTGCACCTCCGACCACCCTTAGGCTAGGGA TAACAGGGTAAT 3' (SEQ ID NO:35)
AG017:S2: 5' CAGCAGAGTTCGAAAACGCAGTTG TGTATAGATCAATGCCCAAGTACTCATCGAGGC ATGCAAGCTTAGATCT 3' (SEQ ID NO:36)
AG018:S1: 5' ACTTCTTCAAGCTTTATGAGCCGTGGT CTATTGGGCAAAATGCCGCAAGCTAGGGATAAC AGGGTAAT 3' (SEQ ID NO:37)
AG018:S2: 5' GGTATCGGCACAGCCTTTGAACCGGCT TTAGGAGAAAGGATTGCAGTTCAGGCATGCAAG CTTAGATCT 3' (SEQ ID NO:38)
AG019:S1: 5' GAGGACTACGACAGGTTGCGGCCG TTGTCGTACCCGTCGACGGACGTGTTTCTCGTG TGCTTCAGCGGCTAGGGATAACAGGGTAAT 3' (SEQ ID NO:39)
AG019:S2: 5' GCAGGGTACGCCCGGGCAGTGGTG ATGTACCTCGGGGAACCACTTCTCCTTGACGTT CTCGAACGACAGGCATGCAAGCTTAGATCT 3' (SEQ ID NO:40)
AG020:S1: 5' GCATAGAACATGCACTACATGCAACAG CAGGGACCATGCCTGCACCAGACGCTAGGGATA ACAGGGTAAT 3' (SEQ ID NO:41)
AG020:S2: 5' GAACATAGACACTGGAATATCCG AGGGTGTGAGGTAGACGTCATTTCGAGAGGCAT GCAAGCTTAGATCT 3' (SEQ ID NO:42)
AG021:S1: 5' CTCCTCACTTGGAGTGGGGTACCA CGGGAAGGCGCCAAAGTTCAACGCTAGGGATAA CAGGGTAAT 3' (SEQ ID NO:43)
AG021:S2: 5' CTGGTGATGCTGGAGTGCTTGGGATTG TGGCTGCGTCTGCGCTGGCAGGCATGCAAGCTT AGATCT 3' (SEQ ID NO:44)

Example 2

Expression of Recombinant AG012, AG013, AG014 AG015, AG016, AG017, AG018, AG019, AG020, or AG021 Protein in Heterologous Expression Systems The coding region of the protein, corresponding to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, is subcloned into previously described expression vectors, and transformed into E. coli using the manufacturer's conditions. Specific examples include plasmids such as pBluescript (Stratagene, La Jolla, Calif.), the pET vector system (Novagen, Inc., Madison, Wis.) pFLAG (International Biotechnologies, Inc., New Haven, Conn.), and pTrcHis (Invitrogen, La Jolla, Calif.). E. coli is cultured, and expression of the AG012, AG013, AG014, AG015, AG016, AG017, AG018, AG019, AG020, or AG021 activity is confirmed. Alternatively, eukaryotic expression systems such as cultured insect cells infected with specific viruses may be preferred. Examples of vectors and insect cell lines are described previously. Protein conferring AG012, AG013, AG014, AG015, AG016, AG017, AG018, AG019, AG020, or AG021 activity is isolated using standard techniques.

Example 3
In vitro Recombination of AG012, AG013, AG014, AG015, AG016, AG017, AG018, AG019, AG020, or AG021 Genes by DNA Shuffling The nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 is amplified by PCR. The resulting DNA fragment is digested by DNaseI treatment essentially as described (Stemmer et al. (1 994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, and transformed into a bacterial strain deficient in AG012, AG013, AG014, AG015, AG016, AG017, AG018, AG019, AG020, or AG021 activity by electroporation using the Biorad Gene Pulser and the manufacturer's conditions. The transformed bacteria are grown on medium that contains inhibitory concentrations of an inhibitor of AG012, AG013, AG014, AG015, AG016, AG017, AG018, AG019, AG020, or AG021 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined. Alternatively, the DNA fragments are cloned into expression vectors for transient or stable transformation into fungal cells, which are screened for differential survival and/or growth in the presence of an inhibitor of AG012, AG013, AG014, AG015, AG016, AG017, AG018, AG019, AG020, or AG021 activity. In a similar reaction, PCR-amplified DNA fragments comprising the Ashbya AG012, AG013, AG014, AG015, AG016, AG017, AG018, AG019, AG020, or AG021 gene encoding the protein and PCR-amplified DNA fragments derived from or comprising another AG012, AG013, AG014, AG015, AG016, AG017, AG018, AG019, AG020, or AG021, gene are recombined in vitro and resulting variants with improved tolerance to the inhibitor are recovered as described above.

Example 4
In vitro Recombination of AG012, AG013, AG014, AG015, AG016, AG017, AG018, AG019, AG020, or AG021 Genes by Staggered Extension Process The Ashbya AG012, AG013, AG014, AG015, AG016, AG017, AG018, AG019, AG020, or AG021 gene encoding the AG012, AG013, AG014, AG015, AG016, AG017, AG018, AG019, AG020, or AG021 protein and another AG012, AG013, AG014, AG015, AG016, AG017, AG018, AG019, AG020, or AG021 gene, or homologs thereof, or fragments thereof, are each cloned into the polylinker of a pBluescript vector. A PCR reaction is carried out essentially as described (Zhao et al. (1998) Nature Biotechnology 16: 258–261) using the "reverse primer" and the "M13-20 primer" (Stratagene Catalog). Amplified PCR fragments are digested with appropriate restriction enzymes and cloned into pTRC99a and mutated AG012, AG013, AG014, AG015, AG016, AG017, AG018, AG019, AG020, or AG021 genes are screened as described in Example 3.

Example 5
In Vitro Binding Assays

Recombinant AG012, AG013, AG014, AG015, AG016, AG017, AG018, AG019, AG020, or AG021 protein is obtained, for example, according to Example 2. The protein is immobilized on chips appropriate for ligand binding assays using techniques which are well known in the art. The protein immobilized on the chip is exposed to sample compound in solution according to methods well know in the art. While the sample compound is in contact with the immobilized protein measurements capable of detecting protein-ligand interactions are conducted. Examples of such measurements are SELDI, biacore and FCS, described above. Compounds found to bind the protein are readily discovered in this fashion and are subjected to further characterization.

Example 6
Cell-Based Assay

Simple cell-based assays are developed to screen for compounds that affect normal functioning of the specific fungal-encoded activity. Such compounds are promising in vitro leads that can be tested for in vivo fungicidal activity. A nucleic acid sequence of the invention according to any one of the sequences SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19, is operably linked to a strong inducible promoter, e.g. GAL1 promoter, GAL10 promoter, or other such promoters known in the art. In one embodiment, overexpression of the essential fungal gene confers upon the fungal cells a greater degree of resistance to an inhibitory compound than is attainable in the wild type fungus. Wild type fungal cells are cultured in 96 well microtiter plates (e.g. 100 ul volume per well) in the presence of a defined concentration of a different chemical compound in each well. Likewise, transgenic fungal cells overexpressing the essential fungal gene (i.e. under inducing conditions) are challenged with the same set of chemical compounds at the same defined concentration. Situations in which growth of the wild type fungus, but not the transgenic fungus, is inhibited by a given compound are identified as prospective situations in which overexpression of the particular gene confers resistance to the inhibitory effect of the test compound. Follow up experiments are carried out to repeat this result with a variety of concentrations of the identified compounds.

In another embodiment, induced overexpression of the essential fungal gene has deleterious effects upon growth or viability of the fungal cells. In this instance, transgenic fungal cells in which the essential fungal gene is operably linked to an inducible promoter are cultured in 96 well microtiter plates in the presence of a defined concentration of a different chemical test compound in each well. After a short incubation period, cells are shifted to full inducing conditions (for example by adding an inducing compound to each well). Normally this induced overexpression would lead to growth arrest of the culture, but, in wells containing inhibitors of the essential fungal gene, growth would proceed and would be monitored via the increased turbidity within such wells.

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleotide sequence consisting essentially of SEQ ID NO:11.

2. The isolated nucleotide sequence of claim 1, wherein the nucleotide sequence is SEQ ID NO:11.

3. The isolated nucleotide sequence of claim 1, wherein the nucleotide sequence is a fungal nucleotide sequence.

4. The isolated nucleotide sequence of claim 1, wherein the nucleotide sequence encodes an amino acid sequence consisting essentially of SEQ ID NO:12.

5. A chimeric gene comprising a promoter operably linked to a nucleotide sequence according to claim 1.

6. The isolated nucleotide sequence of claim 3, wherein the fungus is *Ashbya gossypii*.

7. The chimeric gene of claim 5 wherein the promoter is an inducible promoter.

8. A recombinant vector comprising a chimeric gene according to claim 5 wherein said vector is capable of being stably transformed into a host cell.

9. A host cell comprising the vector according to claim 8, wherein the nucleotide sequence is expressible in the host cell.

10. The host cell according to claim 9, wherein the host cell is eukaryotic.

11. The host cell according to claim 9, wherein the host cell is selected from the group consisting of a yeast cell and a fungal cell.

12. The host cell according to claim 9 wherein the host cell is a prokaryotic cell.

13. The host cell according to claim 11, wherein the host cell is a filamentous fungal cell.

14. The host cell according to claim 12 wherein the host cell is a bacterial cell.

15. The host cell according to claim 13, wherein the host cell is an *Ashbya gossypii* cell.

16. An isolated nucleotide sequence encoding an amino acid sequence according to SEQ ID NO:12.

* * * * *

SEQUENCE LISTING

<160> NUMBER OF SEQ ID NOS: 44

<210> SEQ ID NO 1
<211> LENGTH: 1575
<212> TYPE: DNA
<213> ORGANISM: Ashbya gossypii
<220> FEATURE:
<221> NAME/KEY: CDS
<222> LOCATION: (1)..(1575)

<400> SEQUENCE: 1

| | | | | | | | | | | | | | | | | |
|---|---|---|---|---|---|---|---|---|---|---|---|---|---|---|---|---|
| atg | gcg | ttc | atg | ttc | aag | cca | cca | gag | cag | cgg | aag | cgc | aat | gag | aag | 48 |
| Met | Ala | Phe | Met | Phe | Lys | Pro | Pro | Glu | Gln | Arg | Lys | Arg | Asn | Glu | Lys | |
| 1 | | | | 5 | | | | | 10 | | | | | 15 | | |
| tct | ccg | aga | ttg | tcg | ctg | ccg | tcg | acg | tta | att | ggt | agt | gct | acc | cct | 96 |
| Ser | Pro | Arg | Leu | Ser | Leu | Pro | Ser | Thr | Leu | Ile | Gly | Ser | Ala | Thr | Pro | |
| | | | 20 | | | | | 25 | | | | | 30 | | | |
| gcg | ggc | gac | gaa | cac | gca | tca | gga | gcg | atg | ggc | aac | tca | att | ggg | tcg | 144 |
| Ala | Gly | Asp | Glu | His | Ala | Ser | Gly | Ala | Met | Gly | Asn | Ser | Ile | Gly | Ser | |
| | 35 | | | | | 40 | | | | | 45 | | | | | |
| gat | cta | cac | agg | gag | cag | aaa | ctg | cgt | gga | ctt | ggg | caa | tct | gta | cag | 192 |
| Asp | Leu | His | Arg | Glu | Gln | Lys | Leu | Arg | Gly | Leu | Gly | Gln | Ser | Val | Gln | |
| 50 | | | | | 55 | | | | | 60 | | | | | | |
| ata | gca | gaa | cag | cta | tct | gct | gga | tct | acg | gat | act | ggg | ggg | tcg | gac | 240 |
| Ile | Ala | Glu | Gln | Leu | Ser | Ala | Gly | Ser | Thr | Asp | Thr | Gly | Gly | Ser | Asp | |
| 65 | | | | | 70 | | | | | 75 | | | | | 80 | |
| gtt | ctc | tcg | cag | cac | gcg | cca | tct | agc | gca | tcg | tcg | cag | acc | tcg | aag | 288 |
| Val | Leu | Ser | Gln | His | Ala | Pro | Ser | Ser | Ala | Ser | Ser | Gln | Thr | Ser | Lys | |
| | | | | 85 | | | | | 90 | | | | | 95 | | |
| gtc | ctt | ccc | cgg | cgg | cct | gtg | ccg | ccg | ggg | atg | cct | gcg | ctg | gcg | ttt | 336 |
| Val | Leu | Pro | Arg | Arg | Pro | Val | Pro | Pro | Gly | Met | Pro | Ala | Leu | Ala | Phe | |
| | | | 100 | | | | | 105 | | | | | 110 | | | |
| ctg | tcg | aag | cac | ccg | tac | gca | cag | cag | gtg | acg | ggg | ccg | ctg | ccc | acg | 384 |
| Leu | Ser | Lys | His | Pro | Tyr | Ala | Gln | Gln | Val | Thr | Gly | Pro | Leu | Pro | Thr | |
| | | 115 | | | | | 120 | | | | | 125 | | | | |
| acg | agc | gga | gag | aag | gcg | gga | agt | cac | tca | ggt | gca | acc | acg | ctg | tcc | 432 |
| Thr | Ser | Gly | Glu | Lys | Ala | Gly | Ser | His | Ser | Gly | Ala | Thr | Thr | Leu | Ser | |
| | 130 | | | | | 135 | | | | | 140 | | | | | |
| gcg | ggg | cca | acc | agg | cct | tcg | ctg | ccc | aag | ttg | ccg | tac | ctg | cac | gtg | 480 |
| Ala | Gly | Pro | Thr | Arg | Pro | Ser | Leu | Pro | Lys | Leu | Pro | Tyr | Leu | His | Val | |
| 145 | | | | | 150 | | | | | 155 | | | | | 160 | |
| gag | ccg | aag | ctg | ccc | tgc | gag | gag | ctg | ccg | tac | tct | gcg | ctg | cac | gcg | 528 |
| Glu | Pro | Lys | Leu | Pro | Cys | Glu | Glu | Leu | Pro | Tyr | Ser | Ala | Leu | His | Ala | |
| | | | | 165 | | | | | 170 | | | | | 175 | | |
| ggc | tcg | agc | tca | tcc | agc | aac | ata | cat | tcc | ccg | tcg | cgc | gca | ttg | cag | 576 |
| Gly | Ser | Ser | Ser | Ser | Asn | Ile | His | Ser | Pro | Ser | Arg | Ala | Leu | Gln | | |
| | | | 180 | | | | | 185 | | | | | 190 | | | |
| gag | atg | cgg | tta | atc | tct | gct | ggc | agt | act | ccg | gtt | gag | ccg | gtg | ccc | 624 |
| Glu | Met | Arg | Leu | Ile | Ser | Ala | Gly | Ser | Thr | Pro | Val | Glu | Pro | Val | Pro | |
| | | 195 | | | | | 200 | | | | | 205 | | | | |
| ccg | gcg | gcg | act | gta | ccg | cca | tgc | aaa | gac | gtg | gac | gaa | ttg | gag | gaa | 672 |
| Pro | Ala | Ala | Thr | Val | Pro | Pro | Cys | Lys | Asp | Val | Asp | Glu | Leu | Glu | Glu | |
| | 210 | | | | | 215 | | | | | 220 | | | | | |
| gag | atg | tgg | acg | cat | gtg | cac | ctg | aaa | gac | cag | ata | gaa | gag | ctt | ggc | 720 |
| Glu | Met | Trp | Thr | His | Val | His | Leu | Lys | Asp | Gln | Ile | Glu | Glu | Leu | Gly | |
| 225 | | | | | 230 | | | | | 235 | | | | | 240 | |
| gtg | ctg | ggc | gag | ggc | gcg | ggc | gga | tca | gtc | acg | aag | tgc | aaa | ctt | agg | 768 |
| Val | Leu | Gly | Glu | Gly | Ala | Gly | Gly | Ser | Val | Thr | Lys | Cys | Lys | Leu | Arg | |
| | | | | 245 | | | | | 250 | | | | | 255 | | |

-continued

```
cac ggt tcc aaa atc ttc gcg ctc aaa act ata acc acg ctg acc acg      816
His Gly Ser Lys Ile Phe Ala Leu Lys Thr Ile Thr Thr Leu Thr Thr
            260                 265                 270 gac cag gag agc cag aag cag ata ttc cgc gag ctg cag ttc aac aag      864
Asp Gln Glu Ser Gln Lys Gln Ile Phe Arg Glu Leu Gln Phe Asn Lys
                275                 280                 285 agc tgc aag tct gac tac atc gtg cgc tac tac ggc atg ttt acc gac      912
Ser Cys Lys Ser Asp Tyr Ile Val Arg Tyr Tyr Gly Met Phe Thr Asp
        290                 295                 300 gag gag cac tcc tcg ata tac atc gcc atg gaa tac atg ggc ggg agg      960
Glu Glu His Ser Ser Ile Tyr Ile Ala Met Glu Tyr Met Gly Gly Arg
305                 310                 315                 320 tcg ctg gac gcc atc tac aaa cac cta cta aaa cac ggc ggc agg gtc     1008
Ser Leu Asp Ala Ile Tyr Lys His Leu Leu Lys His Gly Gly Arg Val
                325                 330                 335 ggc gag aag gtg ctc ggc aag atc gcc gaa agc gtg ctg cgc ggc ctg     1056
Gly Glu Lys Val Leu Gly Lys Ile Ala Glu Ser Val Leu Arg Gly Leu
            340                 345                 350 tcg tac ctc cac cag cgc aaa atc atc cac cgc gac atc aag ccc caa     1104
Ser Tyr Leu His Gln Arg Lys Ile Ile His Arg Asp Ile Lys Pro Gln
                355                 360                 365 aac att ctc ctc aac gag gca ggc cag gtg aag ctc tgc gac ttc ggc     1152
Asn Ile Leu Leu Asn Glu Ala Gly Gln Val Lys Leu Cys Asp Phe Gly
        370                 375                 380 gtg agc ggc gag gct gtc aac tcg ctc gcc act acg ttt act ggc acc     1200
Val Ser Gly Glu Ala Val Asn Ser Leu Ala Thr Thr Phe Thr Gly Thr
385                 390                 395                 400 tcg tac tac atg gcg ccg gag cgc atc cag ggc cag cct tac agc gtc     1248
Ser Tyr Tyr Met Ala Pro Glu Arg Ile Gln Gly Gln Pro Tyr Ser Val
                405                 410                 415 acc agc gac gtc tgg tcg ctg ggc ctc acc ctg ctg gag gta gcc cag     1296
Thr Ser Asp Val Trp Ser Leu Gly Leu Thr Leu Leu Glu Val Ala Gln
            420                 425                 430 gcc cac ttc ccc ttc gac tcc ggc aaa ttc gca gcc aac atg ccg ccc     1344
Ala His Phe Pro Phe Asp Ser Gly Lys Phe Ala Ala Asn Met Pro Pro
                435                 440                 445 ata gaa ttg ctt atg ctg atc ctc acc ttc acg ccg cag ctc aaa gat     1392
Ile Glu Leu Leu Met Leu Ile Leu Thr Phe Thr Pro Gln Leu Lys Asp
        450                 455                 460 gaa ccc gag gcg aac atc gtg tgg agc aag gcc ttc aag tca ttc atc     1440
Glu Pro Glu Ala Asn Ile Val Trp Ser Lys Ala Phe Lys Ser Phe Ile
465                 470                 475                 480 agc tac tgt ctc aag aag gag tcg cgc gag cgg ccc tcg ccc agg cag     1488
Ser Tyr Cys Leu Lys Lys Glu Ser Arg Glu Arg Pro Ser Pro Arg Gln
                485                 490                 495 atg ctg cgc cac ccc tgg ata cag ggg cag atg aaa aag cgt gtc aat     1536
Met Leu Arg His Pro Trp Ile Gln Gly Gln Met Lys Lys Arg Val Asn
            500                 505                 510 atg gag aag ttc atc tac aag tgc tgg cag gcc agg tga               1575
Met Glu Lys Phe Ile Tyr Lys Cys Trp Gln Ala Arg
                515                 520                 525
```

<210> SEQ ID NO 2
<211> LENGTH: 524
<212> TYPE: PRT
<213> ORGANISM: Ashbya gossypii

<400> SEQUENCE: 2

```
Met Ala Phe Met Phe Lys Pro Pro Glu Gln Arg Lys Arg Asn Glu Lys
  1               5                  10                  15
```

```
Ser Pro Arg Leu Ser Leu Pro Ser Thr Leu Ile Gly Ser Ala Thr Pro
         20                  25                  30

Ala Gly Asp Glu His Ala Ser Gly Ala Met Gly Asn Ser Ile Gly Ser
         35                  40                  45

Asp Leu His Arg Glu Gln Lys Leu Arg Gly Leu Gly Gln Ser Val Gln
         50                  55                  60

Ile Ala Glu Gln Leu Ser Ala Gly Ser Thr Asp Thr Gly Gly Ser Asp
 65                  70                  75                  80

Val Leu Ser Gln His Ala Pro Ser Ser Ala Ser Ser Gln Thr Ser Lys
                 85                  90                  95

Val Leu Pro Arg Arg Pro Val Pro Pro Gly Met Pro Ala Leu Ala Phe
             100                 105                 110

Leu Ser Lys His Pro Tyr Ala Gln Gln Val Thr Gly Pro Leu Pro Thr
         115                 120                 125

Thr Ser Gly Glu Lys Ala Gly Ser His Ser Gly Ala Thr Thr Leu Ser
         130                 135                 140

Ala Gly Pro Thr Arg Pro Ser Leu Pro Lys Leu Pro Tyr Leu His Val
145                 150                 155                 160

Glu Pro Lys Leu Pro Cys Glu Glu Leu Pro Tyr Ser Ala Leu His Ala
                 165                 170                 175

Gly Ser Ser Ser Ser Asn Ile His Ser Pro Ser Arg Ala Leu Gln
             180                 185                 190

Glu Met Arg Leu Ile Ser Ala Gly Ser Thr Pro Val Glu Pro Val Pro
         195                 200                 205

Pro Ala Ala Thr Val Pro Pro Cys Lys Asp Val Asp Glu Leu Glu Glu
         210                 215                 220

Glu Met Trp Thr His Val His Leu Lys Asp Gln Ile Glu Glu Leu Gly
225                 230                 235                 240

Val Leu Gly Glu Gly Ala Gly Gly Ser Val Thr Lys Cys Lys Leu Arg
                 245                 250                 255

His Gly Ser Lys Ile Phe Ala Leu Lys Thr Ile Thr Thr Leu Thr Thr
             260                 265                 270

Asp Gln Glu Ser Gln Lys Gln Ile Phe Arg Glu Leu Gln Phe Asn Lys
         275                 280                 285

Ser Cys Lys Ser Asp Tyr Ile Val Arg Tyr Tyr Gly Met Phe Thr Asp
         290                 295                 300

Glu Glu His Ser Ser Ile Tyr Ile Ala Met Glu Tyr Met Gly Gly Arg
305                 310                 315                 320

Ser Leu Asp Ala Ile Tyr Lys His Leu Leu Lys His Gly Gly Arg Val
                 325                 330                 335

Gly Glu Lys Val Leu Gly Lys Ile Ala Glu Ser Val Leu Arg Gly Leu
             340                 345                 350

Ser Tyr Leu His Gln Arg Lys Ile Ile His Arg Asp Ile Lys Pro Gln
         355                 360                 365

Asn Ile Leu Leu Asn Glu Ala Gly Gln Val Lys Leu Cys Asp Phe Gly
         370                 375                 380

Val Ser Gly Glu Ala Val Asn Ser Leu Ala Thr Thr Phe Thr Gly Thr
385                 390                 395                 400

Ser Tyr Tyr Met Ala Pro Glu Arg Ile Gln Gly Gln Pro Tyr Ser Val
                 405                 410                 415

Thr Ser Asp Val Trp Ser Leu Gly Leu Thr Leu Leu Glu Val Ala Gln
             420                 425                 430

Ala His Phe Pro Phe Asp Ser Gly Lys Phe Ala Ala Asn Met Pro Pro
```

```
                       435                 440                 445
         Ile Glu Leu Leu Met Leu Ile Leu Thr Phe Thr Pro Gln Leu Lys Asp
                  450                 455                 460

Glu Pro Glu Ala Asn Ile Val Trp Ser Lys Ala Phe Lys Ser Phe Ile
         465                 470                 475                 480

Ser Tyr Cys Leu Lys Lys Glu Ser Arg Glu Arg Pro Ser Pro Arg Gln
                           485                 490                 495

Met Leu Arg His Pro Trp Ile Gln Gly Gln Met Lys Lys Arg Val Asn
                       500                 505                 510

Met Glu Lys Phe Ile Tyr Lys Cys Trp Gln Ala Arg
                       515                 520

<210> SEQ ID NO 3
<211> LENGTH: 1326
<212> TYPE: DNA
<213> ORGANISM: Ashbya gossypii
<220> FEATURE:
<221> NAME/KEY: CDS
<222> LOCATION: (1)..(1326)

<400> SEQUENCE: 3 atg ggg aag gtt gtt caa tta ttc aca cac cca ctg gag ctg aag gca        48
Met Gly Lys Val Val Gln Leu Phe Thr His Pro Leu Glu Leu Lys Ala
  1               5                  10                  15 gct ctg aag ctc aaa ttt ctg agg gaa ccg ctt tat cct gcg gac gac        96
Ala Leu Lys Leu Lys Phe Leu Arg Glu Pro Leu Tyr Pro Ala Asp Asp
                 20                  25                  30 acg cag ggc tct gca gag ctc aag cgg tgc tac cag ctg cta cag cgg       144
Thr Gln Gly Ser Ala Glu Leu Lys Arg Cys Tyr Gln Leu Leu Gln Arg
             35                  40                  45 act tcg agg tct ttt gcg gcc gtg ata atg gag cta cat ccc gag ctg       192
Thr Ser Arg Ser Phe Ala Ala Val Ile Met Glu Leu His Pro Glu Leu
         50                  55                  60 cgc aac gcg gtg atg ctg ttc tac ctg att ctg cgt gcg ctg gat act       240
Arg Asn Ala Val Met Leu Phe Tyr Leu Ile Leu Arg Ala Leu Asp Thr
 65                  70                  75                  80 gtt gaa gac gat atg acg atc agt ccc aag gta aag gtg ccg cta ctc       288
Val Glu Asp Asp Met Thr Ile Ser Pro Lys Val Lys Val Pro Leu Leu
                 85                  90                  95 cgg gag ttc gac cag aaa ctg aag ctg gat acg tgg agt ttc gac ggc       336
Arg Glu Phe Asp Gln Lys Leu Lys Leu Asp Thr Trp Ser Phe Asp Gly
                100                 105                 110 aac gcg aag acg gag aag gac cgt gac gtg ctg gtg gag ttc agc acg       384
Asn Ala Lys Thr Glu Lys Asp Arg Asp Val Leu Val Glu Phe Ser Thr
            115                 120                 125 att cta gcc gag ttc cac aag ctg aag ccc gag tac cag cag gtg att       432
Ile Leu Ala Glu Phe His Lys Leu Lys Pro Glu Tyr Gln Gln Val Ile
        130                 135                 140 gca gac atc aca cac aag atg ggc aac ggc atg gca gac tac att ctg       480
Ala Asp Ile Thr His Lys Met Gly Asn Gly Met Ala Asp Tyr Ile Leu
145                 150                 155                 160 gac gag aag ttt aat ttg agc ggg ttg gag acg atc cag gac tac gac       528
Asp Glu Lys Phe Asn Leu Ser Gly Leu Glu Thr Ile Gln Asp Tyr Asp
                165                 170                 175 cgc tac tgc cac tat gtt gca ggg ctc gtt gga gac ggg cta acc cat       576
Arg Tyr Cys His Tyr Val Ala Gly Leu Val Gly Asp Gly Leu Thr His
            180                 185                 190 ttg atc atg ctg gcg aaa ttc agc agt ccg ggc ctg tat tat gac tct       624
Leu Ile Met Leu Ala Lys Phe Ser Ser Pro Gly Leu Tyr Tyr Asp Ser
        195                 200                 205
```

```
ccc gac ctc tac gag agc atg ggg ctt ttc ctc cag aag acg aac att        672
Pro Asp Leu Tyr Glu Ser Met Gly Leu Phe Leu Gln Lys Thr Asn Ile
    210                 215                 220 atc aga gac tac gcg gag gac ctg gca gac ggg cgc tcg ttc tgg cca        720
Ile Arg Asp Tyr Ala Glu Asp Leu Ala Asp Gly Arg Ser Phe Trp Pro
225                 230                 235                 240 aag gaa atc tgg tca cat tac gca gat gac ctg gcc agt ttt tcg aag        768
Lys Glu Ile Trp Ser His Tyr Ala Asp Asp Leu Ala Ser Phe Ser Lys
                245                 250                 255 cct gaa aat gct acc gct ggc gtt tac tgt atc aac cac ctc gtc ctg        816
Pro Glu Asn Ala Thr Ala Gly Val Tyr Cys Ile Asn His Leu Val Leu
            260                 265                 270 aac gcg cta ggc cac gtc cag cac gtc ctc acg tac ctt gct tct ttg        864
Asn Ala Leu Gly His Val Gln His Val Leu Thr Tyr Leu Ala Ser Leu
        275                 280                 285 agg gag cag tcc tcc ttc cag ttt tgc gcg ata ccc cag gta atg gcc        912
Arg Glu Gln Ser Ser Phe Gln Phe Cys Ala Ile Pro Gln Val Met Ala
    290                 295                 300 att gcg aca ttg gcg ctt gtg ttt ggg aat gag cgc gtg ctc caa aca        960
Ile Ala Thr Leu Ala Leu Val Phe Gly Asn Glu Arg Val Leu Gln Thr
305                 310                 315                 320 agc gtg aaa atc aga aag ggt acg act tgt tat cta att tta aag tcc       1008
Ser Val Lys Ile Arg Lys Gly Thr Thr Cys Tyr Leu Ile Leu Lys Ser
                325                 330                 335 cgc acc ttc caa gga tgt gtg gag atc ttt gaa cac tat ctg cgc gac       1056
Arg Thr Phe Gln Gly Cys Val Glu Ile Phe Glu His Tyr Leu Arg Asp
            340                 345                 350 atc cgg aag cgc ctg act gtt gcc gac ccc aat tac ctg aag cta aat       1104
Ile Arg Lys Arg Leu Thr Val Ala Asp Pro Asn Tyr Leu Lys Leu Asn
        355                 360                 365 att gaa atc gca aag ctt gac aaa ttc att gag gag atg tac cag gat       1152
Ile Glu Ile Ala Lys Leu Asp Lys Phe Ile Glu Glu Met Tyr Gln Asp
    370                 375                 380 aaa ttg ccc gtc ggt gcg aaa cca caa gag acg gaa atc tac aag aag       1200
Lys Leu Pro Val Gly Ala Lys Pro Gln Glu Thr Glu Ile Tyr Lys Lys
385                 390                 395                 400 gtt aga gag aga tca gcg tac gac ctc gag gtc ctg cca cgg gag cag       1248
Val Arg Glu Arg Ser Ala Tyr Asp Leu Glu Val Leu Pro Arg Glu Gln
                405                 410                 415 gag gag gag ttc aag ttt aat gtg ctc ctc tct ata ctc ttt acc gtc       1296
Glu Glu Glu Phe Lys Phe Asn Val Leu Leu Ser Ile Leu Phe Thr Val
            420                 425                 430 ttt ggg gct ctg tac tgg tat gcc aag tga                               1326
Phe Gly Ala Leu Tyr Trp Tyr Ala Lys
        435                 440

<210> SEQ ID NO 4
<211> LENGTH: 441
<212> TYPE: PRT
<213> ORGANISM: Ashbya gossypii

<400> SEQUENCE: 4

Met Gly Lys Val Val Gln Leu Phe Thr His Pro Leu Glu Leu Lys Ala
1               5                   10                  15

Ala Leu Lys Leu Lys Phe Leu Arg Glu Pro Leu Tyr Pro Ala Asp Asp
            20                  25                  30

Thr Gln Gly Ser Ala Glu Leu Lys Arg Cys Tyr Gln Leu Leu Gln Arg
        35                  40                  45

Thr Ser Arg Ser Phe Ala Ala Val Ile Met Glu Leu His Pro Glu Leu
```

|  |  |  | 50 |  |  |  | 55 |  |  |  | 60 |  |
|---|---|---|---|---|---|---|---|---|---|---|---|---|

Arg Asn Ala Val Met Leu Phe Tyr Leu Ile Leu Arg Ala Leu Asp Thr
 65                  70                  75                  80

Val Glu Asp Asp Met Thr Ile Ser Pro Lys Val Lys Val Pro Leu Leu
                 85                  90                  95

Arg Glu Phe Asp Gln Lys Leu Lys Leu Asp Thr Trp Ser Phe Asp Gly
            100                 105                 110

Asn Ala Lys Thr Glu Lys Asp Arg Asp Val Leu Val Glu Phe Ser Thr
            115                 120                 125

Ile Leu Ala Glu Phe His Lys Leu Lys Pro Glu Tyr Gln Gln Val Ile
130                 135                 140

Ala Asp Ile Thr His Lys Met Gly Asn Gly Met Ala Asp Tyr Ile Leu
145                 150                 155                 160

Asp Glu Lys Phe Asn Leu Ser Gly Leu Glu Thr Ile Gln Asp Tyr Asp
                165                 170                 175

Arg Tyr Cys His Tyr Val Ala Gly Leu Val Gly Asp Gly Leu Thr His
            180                 185                 190

Leu Ile Met Leu Ala Lys Phe Ser Ser Pro Gly Leu Tyr Tyr Asp Ser
            195                 200                 205

Pro Asp Leu Tyr Glu Ser Met Gly Leu Phe Leu Gln Lys Thr Asn Ile
210                 215                 220

Ile Arg Asp Tyr Ala Glu Asp Leu Ala Asp Gly Arg Ser Phe Trp Pro
225                 230                 235                 240

Lys Glu Ile Trp Ser His Tyr Ala Asp Asp Leu Ala Ser Phe Ser Lys
                245                 250                 255

Pro Glu Asn Ala Thr Ala Gly Val Tyr Cys Ile Asn His Leu Val Leu
            260                 265                 270

Asn Ala Leu Gly His Val Gln His Val Leu Thr Tyr Leu Ala Ser Leu
            275                 280                 285

Arg Glu Gln Ser Ser Phe Gln Phe Cys Ala Ile Pro Gln Val Met Ala
            290                 295                 300

Ile Ala Thr Leu Ala Leu Val Phe Gly Asn Glu Arg Val Leu Gln Thr
305                 310                 315                 320

Ser Val Lys Ile Arg Lys Gly Thr Thr Cys Tyr Leu Ile Leu Lys Ser
                325                 330                 335

Arg Thr Phe Gln Gly Cys Val Glu Ile Phe Glu His Tyr Leu Arg Asp
            340                 345                 350

Ile Arg Lys Arg Leu Thr Val Ala Asp Pro Asn Tyr Leu Lys Leu Asn
            355                 360                 365

Ile Glu Ile Ala Lys Leu Asp Lys Phe Ile Glu Met Tyr Gln Asp
            370                 375                 380

Lys Leu Pro Val Gly Ala Lys Pro Gln Glu Thr Glu Ile Tyr Lys Lys
385                 390                 395                 400

Val Arg Glu Arg Ser Ala Tyr Asp Leu Glu Val Leu Pro Arg Glu Gln
                405                 410                 415

Glu Glu Glu Phe Lys Phe Asn Val Leu Ser Ile Leu Phe Thr Val
            420                 425                 430

Phe Gly Ala Leu Tyr Trp Tyr Ala Lys
            435                 440

<210> SEQ ID NO 5
<211> LENGTH: 1419
<212> TYPE: DNA
<213> ORGANISM: Ashbya gossypii

```
<220> FEATURE:
<221> NAME/KEY: CDS
<222> LOCATION: (1)..(1419)

<400> SEQUENCE: 5 atg ttt aaa gta act aga agg gcg cgc gtg gca gtc cta gca gcg gtt         48
Met Phe Lys Val Thr Arg Arg Ala Arg Val Ala Val Leu Ala Ala Val
  1               5                  10                  15 ata ggg ttg gcg gtt ctg tcg aca gaa tgg tcg aac cgg agg ttg cat         96
Ile Gly Leu Ala Val Leu Ser Thr Glu Trp Ser Asn Arg Arg Leu His
             20                  25                  30 cgt gtg ttc tgg cgg cag gcg gag ggg ccg ttg gag gtg ccc agc tca        144
Arg Val Phe Trp Arg Gln Ala Glu Gly Pro Leu Glu Val Pro Ser Ser
         35                  40                  45 tac cac gtc ggg gag ctg aac atg cgg gag ttc cgg ggg gcg tgg gag        192
Tyr His Val Gly Glu Leu Asn Met Arg Glu Phe Arg Gly Ala Trp Glu
     50                  55                  60 cgg cgc gac ctg cgg tcg cag ctg gcg gcg cag ttc ccg tac gac acg        240
Arg Arg Asp Leu Arg Ser Gln Leu Ala Ala Gln Phe Pro Tyr Asp Thr
 65                  70                  75                  80 gcg ggg ccg atc cct cgg cgg gtg tgg cag acg tgg aag gtg ccg cgg        288
Ala Gly Pro Ile Pro Arg Arg Val Trp Gln Thr Trp Lys Val Pro Arg
                 85                  90                  95 cac agc gcg cag ttc ccg gag cat ttc cgg agt ctg agc gac gcg tgg        336
His Ser Ala Gln Phe Pro Glu His Phe Arg Ser Leu Ser Asp Ala Trp
            100                 105                 110 gag aac agc gct aag gac gcg gag ggc tac gag tac ttc ctg gtg ggg        384
Glu Asn Ser Ala Lys Asp Ala Glu Gly Tyr Glu Tyr Phe Leu Val Gly
        115                 120                 125 gac gag gat atg ctg ccg ctg ctc gcc aac ctg tat ggg ggc gtg ccg        432
Asp Glu Asp Met Leu Pro Leu Leu Arg Asn Leu Tyr Gly Gly Val Pro
    130                 135                 140 cag gtc ctg cag gcg ttt gag tcg ctg cct ctg gcc atc atg cgc gca        480
Gln Val Leu Gln Ala Phe Glu Ser Leu Pro Leu Ala Ile Met Arg Ala
145                 150                 155                 160 gac ttc ttc cga tac ctg ata ctg tat gca cgc ggc ggt atc tac tct        528
Asp Phe Phe Arg Tyr Leu Ile Leu Tyr Ala Arg Gly Gly Ile Tyr Ser
                165                 170                 175 gac atc gac aca gag ccg ctg cag cca ttg acc gca tgg ccg tcg gtg        576
Asp Ile Asp Thr Glu Pro Leu Gln Pro Leu Thr Ala Trp Pro Ser Val
            180                 185                 190 gac cag gcg gcg ctg cag aag ttt aag aac agg aag gtg cac tac ggg        624
Asp Gln Ala Ala Leu Gln Lys Phe Lys Asn Arg Lys Val His Tyr Gly
        195                 200                 205 ggg aca gag ctg tct gtg ttt ggc gag tcg tcg ttg act ccg ggg ctt        672
Gly Thr Glu Leu Ser Val Phe Gly Glu Ser Ser Leu Thr Pro Gly Leu
    210                 215                 220 gcg ata ggg atc gag gcg gac ccc gac cgg ccc gac tgg tca gag tat        720
Ala Ile Gly Ile Glu Ala Asp Pro Asp Arg Pro Asp Trp Ser Glu Tyr
225                 230                 235                 240 tat gcc agg cgc atc cag ttc tgc caa tgg acg ctc cag gcc aag gcg        768
Tyr Ala Arg Arg Ile Gln Phe Cys Gln Trp Thr Leu Gln Ala Lys Ala
                245                 250                 255 ggc cac ccg ctg ctg cgc gag ctc att ctg aac atc acg ggc acg acg        816
Gly His Pro Leu Leu Arg Glu Leu Ile Leu Asn Ile Thr Gly Thr Thr
            260                 265                 270 ctg cac agt gtc gcc aga agg acg ggc tac gcg cgg ctg ccg ccg gtc        864
Leu His Ser Val Ala Arg Arg Thr Gly Tyr Ala Arg Leu Pro Pro Val
        275                 280                 285 acc ttc gac aca gag cac ctg gag gac tac aac gtg aac tac cgc cac        912
Thr Phe Asp Thr Glu His Leu Glu Asp Tyr Asn Val Asn Tyr Arg His
```

-continued

```
                Thr Phe Asp Thr Glu His Leu Glu Asp Tyr Asn Val Asn Tyr Arg His
                    290                 295                 300 aag aag cgg cac gac gct gcc tac ccg cac acg gag aaa aag acg gcc       960
Lys Lys Arg His Asp Ala Ala Tyr Pro His Thr Glu Lys Lys Thr Ala
305                 310                 315                 320 aag aac aca gac gaa acc gac atc atg aac tgg act ggt cca ggg ata      1008
Lys Asn Thr Asp Glu Thr Asp Ile Met Asn Trp Thr Gly Pro Gly Ile
                325                 330                 335 ttt tcg gac gtg gtt ttc gac tac ctc aac aac ctg ata acc acg aat      1056
Phe Ser Asp Val Val Phe Asp Tyr Leu Asn Asn Leu Ile Thr Thr Asn
            340                 345                 350 gac gaa gta gtg ata tac aat gac aac ttg ctg gaa aag aac ccg gaa      1104
Asp Glu Val Val Ile Tyr Asn Asp Asn Leu Leu Glu Lys Asn Pro Glu
        355                 360                 365 acc ggt gaa ata ttg ccg atc gcg acc tct acg cgc aag ttt gcg gcg      1152
Thr Gly Glu Ile Leu Pro Ile Ala Thr Ser Thr Arg Lys Phe Ala Ala
    370                 375                 380 gaa ata aag aca gca ctc tcg aag tcg aag ccc aag ctt ttc tgg gac      1200
Glu Ile Lys Thr Ala Leu Ser Lys Ser Lys Pro Lys Leu Phe Trp Asp
385                 390                 395                 400 ttt ttc tcc ttg atg cag acg cct gcg ctt ata gat gac gtg gtg gtt      1248
Phe Phe Ser Leu Met Gln Thr Pro Ala Leu Ile Asp Asp Val Val Val
                405                 410                 415 ctt ccg atc acc tcc ttt tcc ccc ggt gtg gga cat atg cag gcg ggc      1296
Leu Pro Ile Thr Ser Phe Ser Pro Gly Val Gly His Met Gln Ala Gly
            420                 425                 430 gag ccc gac cac cct atg gcc ttt gta cac cat cac ttt gag ggc tct      1344
Glu Pro Asp His Pro Met Ala Phe Val His His His Phe Glu Gly Ser
        435                 440                 445 tgg aaa cag cag ggt ccc aaa cac gat gat gac gcg ggg gaa ggg gat      1392
Trp Lys Gln Gln Gly Pro Lys His Asp Asp Asp Ala Gly Glu Gly Asp
    450                 455                 460 aag gca tca gag cat gcg gaa aag tag                                  1419
Lys Ala Ser Glu His Ala Glu Lys
465                 470
```

<210> SEQ ID NO 6
<211> LENGTH: 472
<212> TYPE: PRT
<213> ORGANISM: Ashbya gossypii

<400> SEQUENCE: 6

```
Met Phe Lys Val Thr Arg Arg Ala Arg Val Ala Val Leu Ala Ala Val
  1               5                  10                  15

Ile Gly Leu Ala Val Leu Ser Thr Glu Trp Ser Asn Arg Arg Leu His
                 20                  25                  30

Arg Val Phe Trp Arg Gln Ala Glu Gly Pro Leu Glu Val Pro Ser Ser
             35                  40                  45

Tyr His Val Gly Glu Leu Asn Met Arg Glu Phe Arg Gly Ala Trp Glu
         50                  55                  60

Arg Arg Asp Leu Arg Ser Gln Leu Ala Ala Gln Phe Pro Tyr Asp Thr
 65                  70                  75                  80

Ala Gly Pro Ile Pro Arg Arg Val Trp Gln Thr Trp Lys Val Pro Arg
                 85                  90                  95

His Ser Ala Gln Phe Pro Glu His Phe Arg Ser Leu Ser Asp Ala Trp
            100                 105                 110

Glu Asn Ser Ala Lys Asp Ala Glu Gly Tyr Glu Tyr Phe Leu Val Gly
        115                 120                 125
```

```
Asp Glu Asp Met Leu Pro Leu Leu Arg Asn Leu Tyr Gly Gly Val Pro
    130                 135                 140

Gln Val Leu Gln Ala Phe Glu Ser Leu Pro Leu Ala Ile Met Arg Ala
145                 150                 155                 160

Asp Phe Phe Arg Tyr Leu Ile Leu Tyr Ala Arg Gly Gly Ile Tyr Ser
                165                 170                 175

Asp Ile Asp Thr Glu Pro Leu Gln Pro Leu Thr Ala Trp Pro Ser Val
            180                 185                 190

Asp Gln Ala Ala Leu Gln Lys Phe Lys Asn Arg Lys Val His Tyr Gly
        195                 200                 205

Gly Thr Glu Leu Ser Val Phe Gly Glu Ser Ser Leu Thr Pro Gly Leu
    210                 215                 220

Ala Ile Gly Ile Glu Ala Asp Pro Asp Arg Pro Asp Trp Ser Glu Tyr
225                 230                 235                 240

Tyr Ala Arg Arg Ile Gln Phe Cys Gln Trp Thr Leu Gln Ala Lys Ala
                245                 250                 255

Gly His Pro Leu Leu Arg Glu Leu Ile Leu Asn Ile Thr Gly Thr Thr
            260                 265                 270

Leu His Ser Val Ala Arg Arg Thr Gly Tyr Ala Arg Leu Pro Pro Val
        275                 280                 285

Thr Phe Asp Thr Glu His Leu Glu Asp Tyr Asn Val Asn Tyr Arg His
    290                 295                 300

Lys Lys Arg His Asp Ala Ala Tyr Pro His Thr Glu Lys Lys Thr Ala
305                 310                 315                 320

Lys Asn Thr Asp Glu Thr Asp Ile Met Asn Trp Thr Gly Pro Gly Ile
                325                 330                 335

Phe Ser Asp Val Val Phe Asp Tyr Leu Asn Asn Leu Ile Thr Thr Asn
            340                 345                 350

Asp Glu Val Val Ile Tyr Asn Asp Asn Leu Leu Glu Lys Asn Pro Glu
        355                 360                 365

Thr Gly Glu Ile Leu Pro Ile Ala Thr Ser Thr Arg Lys Phe Ala Ala
    370                 375                 380

Glu Ile Lys Thr Ala Leu Ser Lys Ser Lys Pro Lys Leu Phe Trp Asp
385                 390                 395                 400

Phe Phe Ser Leu Met Gln Thr Pro Ala Leu Ile Asp Asp Val Val Val
                405                 410                 415

Leu Pro Ile Thr Ser Phe Ser Pro Gly Val Gly His Met Gln Ala Gly
            420                 425                 430

Glu Pro Asp His Pro Met Ala Phe Val His His Phe Glu Gly Ser
        435                 440                 445

Trp Lys Gln Gln Gly Pro Lys His Asp Asp Asp Ala Gly Glu Gly Asp
    450                 455                 460

Lys Ala Ser Glu His Ala Glu Lys
465                 470

<210> SEQ ID NO 7
<211> LENGTH: 1089
<212> TYPE: DNA
<213> ORGANISM: Ashbya gossypii
<220> FEATURE:
<221> NAME/KEY: CDS
<222> LOCATION: (1)..(1089)

<400> SEQUENCE: 7 atg tct tca aaa tat gtc aca ttc cgt ggt gcc acg aat ttc cgg cac      48
Met Ser Ser Lys Tyr Val Thr Phe Arg Gly Ala Thr Asn Phe Arg His
```

```
        1               5                    10                   15
aga ata gtg atg gcc act ctg tcg gga aag gct gtg aag att gaa aag      96
Arg Ile Val Met Ala Thr Leu Ser Gly Lys Ala Val Lys Ile Glu Lys
                20                   25                  30 atc agg tcc gag gac atg aat cct ggg ctg cga gac cac gaa gta tcg     144
Ile Arg Ser Glu Asp Met Asn Pro Gly Leu Arg Asp His Glu Val Ser
        35                  40                  45 ttt ctg cgg ctc ata gag gcc gtt acc aat gga agt gta att gag atc     192
Phe Leu Arg Leu Ile Glu Ala Val Thr Asn Gly Ser Val Ile Glu Ile
    50                  55                  60 tcg tac acc ggt acg acc gtg ata tat agg cct gga atc atc gta gga     240
Ser Tyr Thr Gly Thr Thr Val Ile Tyr Arg Pro Gly Ile Ile Val Gly
65                  70                  75                  80 ggg tca cac acg cac aac tgc ccg aat ggc aag gcg gtg ggc tac tac     288
Gly Ser His Thr His Asn Cys Pro Asn Gly Lys Ala Val Gly Tyr Tyr
                85                  90                  95 gtg gag ccg ctc ctg tac ctg gcg cca ttt tct aag aag aag ttt tcg     336
Val Glu Pro Leu Leu Tyr Leu Ala Pro Phe Ser Lys Lys Lys Phe Ser
            100                 105                 110 atc ata ctg cgg ggt gtc acg tcg acg cac cag gac gct ggg ata gag     384
Ile Ile Leu Arg Gly Val Thr Ser Thr His Gln Asp Ala Gly Ile Glu
        115                 120                 125 gcg att aag tgg ggc ctg atg ccc gtg atg gag aag ttc ggt gtg cga     432
Ala Ile Lys Trp Gly Leu Met Pro Val Met Glu Lys Phe Gly Val Arg
    130                 135                 140 gag tgc gct ctc cac acg ctg aag cgc ggg gcg cca ccg ctt ggc ggc     480
Glu Cys Ala Leu His Thr Leu Lys Arg Gly Ala Pro Pro Leu Gly Gly
145                 150                 155                 160 ggt gag gtg cac ctg gtt gtg gac tcg ttg att gcg cag ccg ata aca     528
Gly Glu Val His Leu Val Val Asp Ser Leu Ile Ala Gln Pro Ile Thr
                165                 170                 175 atg cat gct cta gag cgc ccg cta att tcg gcc atc cgt ggc gtc gcc     576
Met His Ala Leu Glu Arg Pro Leu Ile Ser Ala Ile Arg Gly Val Ala
            180                 185                 190 tac tcg acc aga gtc agt ccg tct atg gta aac aga atg atc gat ggc     624
Tyr Ser Thr Arg Val Ser Pro Ser Met Val Asn Arg Met Ile Asp Gly
        195                 200                 205 gct aaa agc gtg ctg aaa cag gtt cca tgc gag gcc aac att act gcg     672
Ala Lys Ser Val Leu Lys Gln Val Pro Cys Glu Ala Asn Ile Thr Ala
    210                 215                 220 gac gtg tgg aga ggc gcg aac tca gga aag agt ccc gga tgg ggc atc     720
Asp Val Trp Arg Gly Ala Asn Ser Gly Lys Ser Pro Gly Trp Gly Ile
225                 230                 235                 240 aca ttg gtg gca gaa act aag aaa ggc tgg agg tac ttc acg gag gcg     768
Thr Leu Val Ala Glu Thr Lys Lys Gly Trp Arg Tyr Phe Thr Glu Ala
                245                 250                 255 atc ggc gac gca ggt gaa gtg cca gag gat att ggg aac aag gca gca     816
Ile Gly Asp Ala Gly Glu Val Pro Glu Asp Ile Gly Asn Lys Ala Ala
            260                 265                 270 tac aac ctt ttg gaa gag atc agt aga agc gcg gtt gtg tgc cgg tcg     864
Tyr Asn Leu Leu Glu Glu Ile Ser Arg Ser Ala Val Val Cys Arg Ser
        275                 280                 285 cag ctg cca cta gca att gtg tac atg gtc att ggg aag gag gat atc     912
Gln Leu Pro Leu Ala Ile Val Tyr Met Val Ile Gly Lys Glu Asp Ile
    290                 295                 300 ggg agg ctc aga ata gcc agg gcc caa gtt gac gaa agc ctg gtc ctc     960
Gly Arg Leu Arg Ile Ala Arg Ala Gln Val Asp Glu Ser Leu Val Leu
305                 310                 315                 320 ctt ttg aga gat atc aaa gaa ctg ttc gga acg gag gcc ctg ctg aaa    1008
```

```
Leu Leu Arg Asp Ile Lys Glu Leu Phe Gly Thr Glu Ala Leu Leu Lys
            325                 330                 335 cct gct gac gat gac acc gac gac ctg atc gtc aca atc aag ggg atc     1056
Pro Ala Asp Asp Asp Thr Asp Asp Leu Ile Val Thr Ile Lys Gly Ile
            340                 345                 350 ggg ttc acg aat acc agc aag aag atc gcc tga                         1089
Gly Phe Thr Asn Thr Ser Lys Lys Ile Ala
            355                 360

<210> SEQ ID NO 8
<211> LENGTH: 362
<212> TYPE: PRT
<213> ORGANISM: Ashbya gossypii

<400> SEQUENCE: 8

Met Ser Ser Lys Tyr Val Thr Phe Arg Gly Ala Thr Asn Phe Arg His
  1               5                  10                  15

Arg Ile Val Met Ala Thr Leu Ser Gly Lys Ala Val Lys Ile Glu Lys
                 20                  25                  30

Ile Arg Ser Glu Asp Met Asn Pro Gly Leu Arg Asp His Glu Val Ser
             35                  40                  45

Phe Leu Arg Leu Ile Glu Ala Val Thr Asn Gly Ser Val Ile Glu Ile
         50                  55                  60

Ser Tyr Thr Gly Thr Thr Val Ile Tyr Arg Pro Gly Ile Ile Val Gly
 65                  70                  75                  80

Gly Ser His Thr His Asn Cys Pro Asn Gly Lys Ala Val Gly Tyr Tyr
                 85                  90                  95

Val Glu Pro Leu Leu Tyr Leu Ala Pro Phe Ser Lys Lys Lys Phe Ser
                100                 105                 110

Ile Ile Leu Arg Gly Val Thr Ser Thr His Gln Asp Ala Gly Ile Glu
            115                 120                 125

Ala Ile Lys Trp Gly Leu Met Pro Val Met Glu Lys Phe Gly Val Arg
        130                 135                 140

Glu Cys Ala Leu His Thr Leu Arg Gly Ala Pro Pro Leu Gly Gly
145                 150                 155                 160

Gly Glu Val His Leu Val Val Asp Ser Leu Ile Ala Gln Pro Ile Thr
                165                 170                 175

Met His Ala Leu Glu Arg Pro Leu Ile Ser Ala Ile Arg Gly Val Ala
            180                 185                 190

Tyr Ser Thr Arg Val Ser Pro Ser Met Val Asn Arg Met Ile Asp Gly
        195                 200                 205

Ala Lys Ser Val Leu Lys Gln Val Pro Cys Glu Ala Asn Ile Thr Ala
225                 230                 235                 240

Asp Val Trp Arg Gly Ala Asn Ser Gly Lys Ser Pro Gly Trp Gly Ile
225                 230                 235                 240

Thr Leu Val Ala Glu Thr Lys Lys Gly Trp Arg Tyr Phe Thr Glu Ala
                245                 250                 255

Ile Gly Asp Ala Gly Glu Val Pro Glu Asp Ile Gly Asn Lys Ala Ala
            260                 265                 270

Tyr Asn Leu Leu Glu Glu Ile Ser Arg Ser Ala Val Val Cys Arg Ser
        275                 280                 285

Gln Leu Pro Leu Ala Ile Val Tyr Met Val Ile Gly Lys Glu Asp Ile
    290                 295                 300

Gly Arg Leu Arg Ile Ala Arg Ala Gln Val Asp Glu Ser Leu Val Leu
305                 310                 315                 320
```

```
Leu Leu Arg Asp Ile Lys Glu Leu Phe Gly Thr Glu Ala Leu Leu Lys
            325                 330                 335

Pro Ala Asp Asp Thr Asp Asp Leu Ile Val Thr Ile Lys Gly Ile
            340                 345                 350

Gly Phe Thr Asn Thr Ser Lys Lys Ile Ala
            355                 360

<210> SEQ ID NO 9
<211> LENGTH: 1941
<212> TYPE: DNA
<213> ORGANISM: Ashbya gossypii
<220> FEATURE:
<221> NAME/KEY: CDS
<222> LOCATION: (1)..(1941)

<400> SEQUENCE: 9 atg gag aat cct cac gta cat gat aat tta caa cac atc cag gcg gtg      48
Met Glu Asn Pro His Val His Asp Asn Leu Gln His Ile Gln Ala Val
  1               5                  10                  15 tta tcg aac tac gac aca tcg ttt ctc tcg gac gat gaa gag gac tac      96
Leu Ser Asn Tyr Asp Thr Ser Phe Leu Ser Asp Asp Glu Glu Asp Tyr
             20                  25                  30 tgt ccg ctc tgc atg gag cct ttg gac atc acc gat aag aac ttt aag     144
Cys Pro Leu Cys Met Glu Pro Leu Asp Ile Thr Asp Lys Asn Phe Lys
         35                  40                  45 ccg tgt ccg tgc ggg tat caa atc tgt cag ttc tgc tac aac aac atc     192
Pro Cys Pro Cys Gly Tyr Gln Ile Cys Gln Phe Cys Tyr Asn Asn Ile
     50                  55                  60 aga cag aac ccg gag cta aat ggg cgg tgt cct gcg tgt cgg cga aag     240
Arg Gln Asn Pro Glu Leu Asn Gly Arg Cys Pro Ala Cys Arg Arg Lys
 65                  70                  75                  80 tat gat gat gag tcg gtg gag tac att gtt ttg agc ccc gag gag ctg     288
Tyr Asp Asp Glu Ser Val Glu Tyr Ile Val Leu Ser Pro Glu Glu Leu
                 85                  90                  95 aaa ctt gag cga gcg aag cag gcg cgg aag gag cgc gag cgc aag cag     336
Lys Leu Glu Arg Ala Lys Gln Ala Arg Lys Glu Arg Glu Arg Lys Gln
            100                 105                 110 cgc gag aag gag cga aag gaa aac gaa tat gcc aac cgc aag cat ctc     384
Arg Glu Lys Glu Arg Lys Glu Asn Glu Tyr Ala Asn Arg Lys His Leu
        115                 120                 125 gcc ggc atg cgc gtt atc cag aag aat ttg gta tac gtt att ggc ctg     432
Ala Gly Met Arg Val Ile Gln Lys Asn Leu Val Tyr Val Ile Gly Leu
    130                 135                 140 aac cca ccc gta ccg tac gag gag gtt ggt gcg ctg ttg cgc tcg gac     480
Asn Pro Pro Val Pro Tyr Glu Glu Val Gly Ala Leu Leu Arg Ser Asp
145                 150                 155                 160 aag tac ttt ggg cag tac ggg aag atc aac aag atc gtc gtg aac cgc     528
Lys Tyr Phe Gly Gln Tyr Gly Lys Ile Asn Lys Ile Val Val Asn Arg
                165                 170                 175 aag aca ggc cac aat gac cac cag acg ggt tat ggg ata tat gtt aca     576
Lys Thr Gly His Asn Asp His Gln Thr Gly Tyr Gly Ile Tyr Val Thr
            180                 185                 190 ttt tcc agg aaa gag gat gct gct cgc tgt ata cag gct gtg gat ggt     624
Phe Ser Arg Lys Glu Asp Ala Ala Arg Cys Ile Gln Ala Val Asp Gly
        195                 200                 205 acg ttt atg gat ggg cgg cag gtg aag gcg gca tac gga acc acg aag     672
Thr Phe Met Asp Gly Arg Gln Val Lys Ala Ala Tyr Gly Thr Thr Lys
    210                 215                 220 tac tgc tcg tct tat ttg cgc gga cag tcg tgc ccc aac ccc aat tgc     720
Tyr Cys Ser Ser Tyr Leu Arg Gly Gln Ser Cys Pro Asn Pro Asn Cys
225                 230                 235                 240
```

```
atg ttc tta cac gag ccg gga gaa gaa gct gat tcc ttt aat aaa cga    768
Met Phe Leu His Glu Pro Gly Glu Glu Ala Asp Ser Phe Asn Lys Arg
            245                 250                 255 gag ctc agt ggc aag cag cag ccg cac cag cag ccg ggc cag cag ttg    816
Glu Leu Ser Gly Lys Gln Gln Pro His Gln Gln Pro Gly Gln Gln Leu
        260                 265                 270 cac cag cac ggt agc cag cat ctt cct tcg cag ttg cag tca tct gtg    864
His Gln His Gly Ser Gln His Leu Pro Ser Gln Leu Gln Ser Ser Val
            275                 280                 285 cac cag ccg gct caa gta cac gtg cac cag cta aat gct cag cct cat    912
His Gln Pro Ala Gln Val His Val His Gln Leu Asn Ala Gln Pro His
        290                 295                 300 att cac cac ccc tcg ccc ttc aag ggt ccc cat aat tcc ggt gct gcg    960
Ile His His Pro Ser Pro Phe Lys Gly Pro His Asn Ser Gly Ala Ala
305                 310                 315                 320 gcg tct aat aac agt aac ggc gcg tcc gct gta ccc tca ccc gca caa   1008
Ala Ser Asn Asn Ser Asn Gly Ala Ser Ala Val Pro Ser Pro Ala Gln
            325                 330                 335 gcc aaa gcc caa cta cac atg gat gac agc tct tcc tct tcg aca ccc   1056
Ala Lys Ala Gln Leu His Met Asp Asp Ser Ser Ser Ser Ser Thr Pro
        340                 345                 350 gct gcg cat acc cca atc ctc act ccc gcg cca tta cca aca ggt gca   1104
Ala Ala His Thr Pro Ile Leu Thr Pro Ala Pro Leu Pro Thr Gly Ala
            355                 360                 365 aac cca tgg ggt atc aca cag tcc tct acc ccc gtc tct gca tta tca   1152
Asn Pro Trp Gly Ile Thr Gln Ser Ser Thr Pro Val Ser Ala Leu Ser
        370                 375                 380 aaa gtg tcg agc tct acc gcg ttc ccg acg tta ggc gag gct ata aat   1200
Lys Val Ser Ser Ser Thr Ala Phe Pro Thr Leu Gly Glu Ala Ile Asn
385                 390                 395                 400 acc cct gcg cct act ttc aat ggt gta cag gcc gcc gcc tcc agt tat   1248
Thr Pro Ala Pro Thr Phe Asn Gly Val Gln Ala Ala Ala Ser Ser Tyr
            405                 410                 415 aac cag aac ggg agc agt aaa aat aaa aag aac aac gat acg aag aat   1296
Asn Gln Asn Gly Ser Ser Lys Asn Lys Lys Asn Asn Asp Thr Lys Asn
        420                 425                 430 tat gaa gat cct tat gac ccc ttg tgc agc gcg gta aaa ttt att gac   1344
Tyr Glu Asp Pro Tyr Asp Pro Leu Cys Ser Ala Val Lys Phe Ile Asp
            435                 440                 445 gat aca att gcc ttt ttg tct gac tat aag tgc gtt tcc tac aat ttg   1392
Asp Thr Ile Ala Phe Leu Ser Asp Tyr Lys Cys Val Ser Tyr Asn Leu
450                 455                 460 aga agc gga ctc att gat gac gca act tat gcc agc tac ccc tct ttg   1440
Arg Ser Gly Leu Ile Asp Asp Ala Thr Tyr Ala Ser Tyr Pro Ser Leu
465                 470                 475                 480 ttt tcc ttt tcc aat atc gac gtt tcc gcg gaa tct gaa ggt ata tta   1488
Phe Ser Phe Ser Asn Ile Asp Val Ser Ala Glu Ser Glu Gly Ile Leu
            485                 490                 495 gga aga aag ctt att gac atg ctt gcg gtt aag cca tgg gat cag gtg   1536
Gly Arg Lys Leu Ile Asp Met Leu Ala Val Lys Pro Trp Asp Gln Val
        500                 505                 510 gcc gcc acc ttc cct gct gta aat gaa atg tcg ccg cag ctc caa cgg   1584
Ala Ala Thr Phe Pro Ala Val Asn Glu Met Ser Pro Gln Leu Gln Arg
            515                 520                 525 caa gtc ctg aga caa caa cag atg gcc act act ccc aaa cag cag cag   1632
Gln Val Leu Arg Gln Gln Gln Met Ala Thr Thr Pro Lys Gln Gln Gln
        530                 535                 540 ctg gtg cag atg cag agg aat aac cca gac cca aac tca caa gta tcc   1680
Leu Val Gln Met Gln Arg Asn Asn Pro Asp Pro Asn Ser Gln Val Ser
```

```
                545                 550                 555                 560
ccc acc agc cag cta cag caa cag cag cta cag cat tct cat tcg cag              1728
Pro Thr Ser Gln Leu Gln Gln Gln Gln Leu Gln His Ser His Ser Gln
                565                 570                 575 tcc cag cag gag cct cca cag gag cca cct ttt tcg cag caa cag cag              1776
Ser Gln Gln Glu Pro Pro Gln Glu Pro Pro Phe Ser Gln Gln Gln Gln
                580                 585                 590 cac aga acc gtc gtt cat act cct ccg cca ggg atg ttt gtc caa aac              1824
His Arg Thr Val Val His Thr Pro Pro Pro Gly Met Phe Val Gln Asn
                595                 600                 605 ggc cag atg tcc cag acg cag tct gta ccg cat atg gtg gcc cag acc              1872
Gly Gln Met Ser Gln Thr Gln Ser Val Pro His Met Val Ala Gln Thr
                610                 615                 620 cgt agt aat aat tct acc gac ctt ctg aac caa ctg att aat ggc aag              1920
Arg Ser Asn Asn Ser Thr Asp Leu Leu Asn Gln Leu Ile Asn Gly Lys
625                 630                 635                 640 aag gtt act gcc ggc act taa                                                  1941
Lys Val Thr Ala Gly Thr
                645
```

<210> SEQ ID NO 10
<211> LENGTH: 646
<212> TYPE: PRT
<213> ORGANISM: Ashbya gossypii

<400> SEQUENCE: 10

```
Met Glu Asn Pro His Val His Asp Asn Leu Gln His Ile Gln Ala Val
  1               5                  10                  15

Leu Ser Asn Tyr Asp Thr Ser Phe Leu Ser Asp Asp Glu Glu Asp Tyr
                 20                  25                  30

Cys Pro Leu Cys Met Glu Pro Leu Asp Ile Thr Asp Lys Asn Phe Lys
             35                  40                  45

Pro Cys Pro Cys Gly Tyr Gln Ile Cys Gln Phe Cys Tyr Asn Asn Ile
         50                  55                  60

Arg Gln Asn Pro Glu Leu Asn Gly Arg Cys Pro Ala Cys Arg Arg Lys
 65                  70                  75                  80

Tyr Asp Asp Glu Ser Val Glu Tyr Ile Val Leu Ser Pro Glu Glu Leu
                 85                  90                  95

Lys Leu Glu Arg Ala Lys Gln Ala Arg Lys Glu Arg Glu Arg Lys Gln
            100                 105                 110

Arg Glu Lys Glu Arg Lys Glu Asn Glu Tyr Ala Asn Arg Lys His Leu
        115                 120                 125

Ala Gly Met Arg Val Ile Gln Lys Asn Leu Val Tyr Val Ile Gly Leu
130                 135                 140

Asn Pro Pro Val Pro Tyr Glu Glu Val Gly Ala Leu Leu Arg Ser Asp
145                 150                 155                 160

Lys Tyr Phe Gly Gln Tyr Gly Lys Ile Asn Lys Ile Val Val Asn Arg
                165                 170                 175

Lys Thr Gly His Asn Asp His Gln Thr Gly Tyr Gly Ile Tyr Val Thr
            180                 185                 190

Phe Ser Arg Lys Glu Asp Ala Ala Arg Cys Ile Gln Ala Val Asp Gly
        195                 200                 205

Thr Phe Met Asp Gly Arg Gln Val Lys Ala Ala Tyr Gly Thr Thr Lys
    210                 215                 220

Tyr Cys Ser Ser Tyr Leu Arg Gly Gln Ser Cys Pro Asn Pro Asn Cys
225                 230                 235                 240
```

-continued

```
Met Phe Leu His Glu Pro Gly Glu Ala Asp Ser Phe Asn Lys Arg
            245                 250                 255

Glu Leu Ser Gly Lys Gln Gln Pro His Gln Gln Pro Gly Gln Gln Leu
            260                 265                 270

His Gln His Gly Ser Gln His Leu Pro Ser Gln Leu Gln Ser Ser Val
            275                 280                 285

His Gln Pro Ala Gln Val His Val His Gln Leu Asn Ala Gln Pro His
        290                 295                 300

Ile His His Pro Ser Pro Phe Lys Gly Pro His Asn Ser Gly Ala Ala
305                 310                 315                 320

Ala Ser Asn Asn Ser Asn Gly Ala Ser Ala Val Pro Ser Pro Ala Gln
                325                 330                 335

Ala Lys Ala Gln Leu His Met Asp Asp Ser Ser Ser Ser Thr Pro
            340                 345                 350

Ala Ala His Thr Pro Ile Leu Thr Pro Ala Pro Leu Pro Thr Gly Ala
            355                 360                 365

Asn Pro Trp Gly Ile Thr Gln Ser Ser Thr Pro Val Ser Ala Leu Ser
370                 375                 380

Lys Val Ser Ser Ser Thr Ala Phe Pro Thr Leu Gly Glu Ala Ile Asn
385                 390                 395                 400

Thr Pro Ala Pro Thr Phe Asn Gly Val Gln Ala Ala Ser Ser Tyr
            405                 410                 415

Asn Gln Asn Gly Ser Ser Lys Asn Lys Lys Asn Asn Asp Thr Lys Asn
            420                 425                 430

Tyr Glu Asp Pro Tyr Asp Pro Leu Cys Ser Ala Val Lys Phe Ile Asp
            435                 440                 445

Asp Thr Ile Ala Phe Leu Ser Asp Tyr Lys Cys Val Ser Tyr Asn Leu
    450                 455                 460

Arg Ser Gly Leu Ile Asp Asp Ala Thr Tyr Ala Ser Tyr Pro Ser Leu
465                 470                 475                 480

Phe Ser Phe Ser Asn Ile Asp Val Ser Ala Glu Ser Glu Gly Ile Leu
            485                 490                 495

Gly Arg Lys Leu Ile Asp Met Leu Ala Val Lys Pro Trp Asp Gln Val
            500                 505                 510

Ala Ala Thr Phe Pro Ala Val Asn Glu Met Ser Pro Gln Leu Gln Arg
            515                 520                 525

Gln Val Leu Arg Gln Gln Gln Met Ala Thr Thr Pro Lys Gln Gln Gln
530                 535                 540

Leu Val Gln Met Gln Arg Asn Asn Pro Asp Pro Asn Ser Gln Val Ser
545                 550                 555                 560

Pro Thr Ser Gln Leu Gln Gln Gln Leu Gln His Ser His Ser Gln
            565                 570                 575

Ser Gln Gln Glu Pro Pro Gln Glu Pro Pro Phe Ser Gln Gln Gln
            580                 585                 590

His Arg Thr Val Val His Thr Pro Pro Gly Met Phe Val Gln Asn
            595                 600                 605

Gly Gln Met Ser Gln Thr Gln Ser Val Pro His Met Val Ala Gln Thr
            610                 615                 620

Arg Ser Asn Asn Ser Thr Asp Leu Leu Asn Gln Leu Ile Asn Gly Lys
625                 630                 635                 640

Lys Val Thr Ala Gly Thr
                645
```

```
<210> SEQ ID NO 11
<211> LENGTH: 1269
<212> TYPE: DNA
<213> ORGANISM: Ashbya gossypii
<220> FEATURE:
<221> NAME/KEY: CDS
<222> LOCATION: (1)..(1269)

<400> SEQUENCE: 11 atg ccg aac tgg ttt gag aga gta ttt tta gca cag aaa ccg cca ggc     48
Met Pro Asn Trp Phe Glu Arg Val Phe Leu Ala Gln Lys Pro Pro Gly
 1               5                  10                  15 tcc cgc ctt gcc aac ctc gag acg agt ttt gat gcg aat cta tca ata     96
Ser Arg Leu Ala Asn Leu Glu Thr Ser Phe Asp Ala Asn Leu Ser Ile
             20                  25                  30 aag agg ctg aag aac cac caa ttc acg ctg aaa gag gtc tgg cac tat    144
Lys Arg Leu Lys Asn His Gln Phe Thr Leu Lys Glu Val Trp His Tyr
         35                  40                  45 ggg ttt cta ggg aag gta ctt ttc ttc gtc ttc ata gcg aat cca aca    192
Gly Phe Leu Gly Lys Val Leu Phe Phe Val Phe Ile Ala Asn Pro Thr
     50                  55                  60 cca tgg ctc ctg aag ggc tgt gtg agc atg cta ttc ctt gca ttg ttt    240
Pro Trp Leu Leu Lys Gly Cys Val Ser Met Leu Phe Leu Ala Leu Phe
 65                  70                  75                  80 ttg atg cct gct acc ggc cag ttt ttc ttc cat gct ctt ccg ata ttc    288
Leu Met Pro Ala Thr Gly Gln Phe Phe Phe His Ala Leu Pro Ile Phe
                 85                  90                  95 aca tgg cta gcg cta tat ttt acc tct gca tct ttc ggc tcc acc tat    336
Thr Trp Leu Ala Leu Tyr Phe Thr Ser Ala Ser Phe Gly Ser Thr Tyr
            100                 105                 110 agg cct ccg atc acc gtg aag gtt ctc cct gcc att gaa acc ata atg    384
Arg Pro Pro Ile Thr Val Lys Val Leu Pro Ala Ile Glu Thr Ile Met
        115                 120                 125 tac ggt gac aat ttg agc gac gtg ttg gca gcg tcg acg aac aag tgc    432
Tyr Gly Asp Asn Leu Ser Asp Val Leu Ala Ala Ser Thr Asn Lys Cys
    130                 135                 140 ttg gat atc ctc gcg tgg ctt ccc tac ggt atc ctt cac ttc ggg gcc    480
Leu Asp Ile Leu Ala Trp Leu Pro Tyr Gly Ile Leu His Phe Gly Ala
145                 150                 155                 160 ccg ttt gtg gtt gcc gca ata ctc ttt atc ttt gca cct ccg acc acc    528
Pro Phe Val Val Ala Ala Ile Leu Phe Ile Phe Ala Pro Pro Thr Thr
                165                 170                 175 ctt aga ggg tat gca ttt gcc ttt ggt tac atc aac cta ttc ggt gtg    576
Leu Arg Gly Tyr Ala Phe Ala Phe Gly Tyr Ile Asn Leu Phe Gly Val
            180                 185                 190 ata atc cag aac ttc ttc cct gcg gcg cct cca tgg tac aag aat ctc    624
Ile Ile Gln Asn Phe Phe Pro Ala Ala Pro Pro Trp Tyr Lys Asn Leu
        195                 200                 205 tat ggt ttg tcc gct gca cac tac ggt atg aag ggc tcg cct ggc ggc    672
Tyr Gly Leu Ser Ala Ala His Tyr Gly Met Lys Gly Ser Pro Gly Gly
    210                 215                 220 cta agc cgt atc gat gag tac ttg ggc att gat cta tac aca act gcg    720
Leu Ser Arg Ile Asp Glu Tyr Leu Gly Ile Asp Leu Tyr Thr Thr Ala
225                 230                 235                 240 ttt tcg aac tct gct gtt atc ttt ggt gca ttt cat tct cta cat tca    768
Phe Ser Asn Ser Ala Val Ile Phe Gly Ala Phe His Ser Leu His Ser
                245                 250                 255 ggc tgt gca act atg gag gcg ctt ttc ttg gca cat gtg ttc cca cgc    816
Gly Cys Ala Thr Met Glu Ala Leu Phe Leu Ala His Val Phe Pro Arg
            260                 265                 270 ttg cgg cta ctg ttc gtc ttt tac gtc tgt tgg cta tgg tgg tct acc    864
```

```
Leu Arg Leu Leu Phe Val Phe Tyr Val Cys Trp Leu Trp Trp Ser Thr
        275                 280                 285 atg tac ctt act cac cat tac ttt gtt gac cta atg gca ggc tca att      912
Met Tyr Leu Thr His His Tyr Phe Val Asp Leu Met Ala Gly Ser Ile
    290                 295                 300 ttg tcg tac gtt att ttt cag tac acc aag tat tgc cac ttg cct atc      960
Leu Ser Tyr Val Ile Phe Gln Tyr Thr Lys Tyr Cys His Leu Pro Ile
305                 310                 315                 320 gtg cat cca gag tat ttt acc aga tgg tcc tat gcc gaa atc aag acg     1008
Val His Pro Glu Tyr Phe Thr Arg Trp Ser Tyr Ala Glu Ile Lys Thr
                325                 330                 335 ttt gac atc atc cag tct gat cca tta tac cac gat tct agt gat gtc     1056
Phe Asp Ile Ile Gln Ser Asp Pro Leu Tyr His Asp Ser Ser Asp Val
            340                 345                 350 gaa gcg ttg cct cta gca ccc ctg gat aca gat ttt aac ttc acg ttt     1104
Glu Ala Leu Pro Leu Ala Pro Leu Asp Thr Asp Phe Asn Phe Thr Phe
        355                 360                 365 gag atg agc tct gtg gat gaa gtt gcg acg ccg aca ccg tcg ata ttt     1152
Glu Met Ser Ser Val Asp Glu Val Ala Thr Pro Thr Pro Ser Ile Phe
370                 375                 380 gat gaa gga gca ccg ggg tca gcc tca aga tct tct gcg aac tcc att     1200
Asp Glu Gly Ala Pro Gly Ser Ala Ser Arg Ser Ser Ala Asn Ser Ile
385                 390                 395                 400 gaa gtg cct gat gct gaa ccg ttc agg gct aat ttt gtg aac aaa atg     1248
Glu Val Pro Asp Ala Glu Pro Phe Arg Ala Asn Phe Val Asn Lys Met
                405                 410                 415 tac agg caa cgt tat gat taa                                         1269
Tyr Arg Gln Arg Tyr Asp
            420

<210> SEQ ID NO 12
<211> LENGTH: 422
<212> TYPE: PRT
<213> ORGANISM: Ashbya gossypii

<400> SEQUENCE: 12

Met Pro Asn Trp Phe Glu Arg Val Phe Leu Ala Gln Lys Pro Gly
  1               5                  10                  15

Ser Arg Leu Ala Asn Leu Glu Thr Ser Phe Asp Ala Asn Leu Ser Ile
             20                  25                  30

Lys Arg Leu Lys Asn His Gln Phe Thr Leu Lys Glu Val Trp His Tyr
         35                  40                  45

Gly Phe Leu Gly Lys Val Leu Phe Val Phe Ile Ala Asn Pro Thr
     50                  55                  60

Pro Trp Leu Leu Lys Gly Cys Val Ser Met Leu Phe Leu Ala Leu Phe
 65                  70                  75                  80

Leu Met Pro Ala Thr Gly Gln Phe Phe His Ala Leu Pro Ile Phe
                 85                  90                  95

Thr Trp Leu Ala Leu Tyr Phe Thr Ser Ala Ser Phe Gly Ser Thr Tyr
            100                 105                 110

Arg Pro Pro Ile Thr Val Lys Val Leu Pro Ala Ile Glu Thr Ile Met
        115                 120                 125

Tyr Gly Asp Asn Leu Ser Asp Val Leu Ala Ala Ser Thr Asn Lys Cys
    130                 135                 140

Leu Asp Ile Leu Ala Trp Leu Pro Tyr Gly Ile Leu His Phe Gly Ala
145                 150                 155                 160

Pro Phe Val Val Ala Ala Ile Leu Phe Ile Phe Ala Pro Pro Thr Thr
                165                 170                 175
```

```
Leu Arg Gly Tyr Ala Phe Ala Phe Gly Tyr Ile Asn Leu Phe Gly Val
            180                 185                 190

Ile Ile Gln Asn Phe Phe Pro Ala Ala Pro Trp Tyr Lys Asn Leu
        195                 200                 205

Tyr Gly Leu Ser Ala Ala His Tyr Gly Met Lys Gly Ser Pro Gly Gly
            210                 215                 220

Leu Ser Arg Ile Asp Glu Tyr Leu Gly Ile Asp Leu Tyr Thr Thr Ala
225                 230                 235                 240

Phe Ser Asn Ser Ala Val Ile Phe Gly Ala Phe His Ser Leu His Ser
                245                 250                 255

Gly Cys Ala Thr Met Glu Ala Leu Phe Leu Ala His Val Phe Pro Arg
            260                 265                 270

Leu Arg Leu Leu Phe Val Phe Tyr Val Cys Trp Leu Trp Trp Ser Thr
            275                 280                 285

Met Tyr Leu Thr His His Tyr Phe Val Asp Leu Met Ala Gly Ser Ile
            290                 295                 300

Leu Ser Tyr Val Ile Phe Gln Tyr Thr Lys Tyr Cys His Leu Pro Ile
305                 310                 315                 320

Val His Pro Glu Tyr Phe Thr Arg Trp Ser Tyr Ala Glu Ile Lys Thr
                325                 330                 335

Phe Asp Ile Ile Gln Ser Asp Pro Leu Tyr His Asp Ser Ser Asp Val
            340                 345                 350

Glu Ala Leu Pro Leu Ala Pro Leu Asp Thr Asp Phe Asn Phe Thr Phe
            355                 360                 365

Glu Met Ser Ser Val Asp Glu Val Ala Thr Pro Thr Pro Ser Ile Phe
            370                 375                 380

Asp Glu Gly Ala Pro Gly Ser Ala Ser Arg Ser Ser Ala Asn Ser Ile
385                 390                 395                 400

Glu Val Pro Asp Ala Glu Pro Phe Arg Ala Asn Phe Val Asn Lys Met
                405                 410                 415

Tyr Arg Gln Arg Tyr Asp
            420

<210> SEQ ID NO 13
<211> LENGTH: 2286
<212> TYPE: DNA
<213> ORGANISM: Ashbya gossypii
<220> FEATURE:
<221> NAME/KEY: CDS
<222> LOCATION: (1)..(2286)

<400> SEQUENCE: 13 atg tcg aac cag gcg tcg caa tcg acc att tcg ctg cgc agc gtg gtt      48
Met Ser Asn Gln Ala Ser Gln Ser Thr Ile Ser Leu Arg Ser Val Val
 1               5                  10                  15 tcg acg gcg aca caa cag ctg atg aac aaa aag gtg tct gag gaa gac      96
Ser Thr Ala Thr Gln Gln Leu Met Asn Lys Lys Val Ser Glu Glu Asp
                20                  25                  30 tcg ctg tac cac atc tgt gtg ggg gtg aag cgc aag ctg gag tgc ttg     144
Ser Leu Tyr His Ile Cys Val Gly Val Lys Arg Lys Leu Glu Cys Leu
            35                  40                  45 ccg cag ctg aag ccg tat ctg gca ctg gca cat gcg aat gcg gcg ctg     192
Pro Gln Leu Lys Pro Tyr Leu Ala Leu Ala His Ala Asn Ala Ala Leu
        50                  55                  60 gcg agt gag caa cag gca gtg ctg ttg gcg cag aag gat gca atg gag     240
Ala Ser Glu Gln Gln Ala Val Leu Leu Ala Gln Lys Asp Ala Met Glu
65                  70                  75                  80
```

```
gcg gct gag gtg ccg ctg agc ccg ctc aac ccg gcg cac aac agc atg      288
Ala Ala Glu Val Pro Leu Ser Pro Leu Asn Pro Ala His Asn Ser Met
                85                  90                  95 atc tct gca tct gca ggg gcg gcg acg tcg cct gtg tct gag ata cgg      336
Ile Ser Ala Ser Ala Gly Ala Ala Thr Ser Pro Val Ser Glu Ile Arg
            100                 105                 110 ccg acg tcg att tcg agc agc aca cta gat gag tct gag gac agc aac      384
Pro Thr Ser Ile Ser Ser Ser Thr Leu Asp Glu Ser Glu Asp Ser Asn
            115                 120                 125 gcg gta aat atg gag gac acc gtc ttg acg ttt gcg atg ggg att ctt      432
Ala Val Asn Met Glu Asp Thr Val Leu Thr Phe Ala Met Gly Ile Leu
        130                 135                 140 cca tcg tcc gtg gag tgc gat ccc gtg acg gag ctg tcg aag ctg ttc      480
Pro Ser Ser Val Glu Cys Asp Pro Val Thr Glu Leu Ser Lys Leu Phe
145                 150                 155                 160 cag cag ggc tcg ccc ctg tgc att atc ttt aat gca gtc aag ccg cac      528
Gln Gln Gly Ser Pro Leu Cys Ile Ile Phe Asn Ala Val Lys Pro His
                165                 170                 175 tgc aaa ctt ccc gtt gtt tcg tct gac gac acg aag ata tgc aaa aag      576
Cys Lys Leu Pro Val Val Ser Ser Asp Asp Thr Lys Ile Cys Lys Lys
            180                 185                 190 tcg atc tac gat ttt att atg ggg ctg aag ctg cat ttt gcg ttc aac      624
Ser Ile Tyr Asp Phe Ile Met Gly Leu Lys Leu His Phe Ala Phe Asn
            195                 200                 205 gac gag gag ctg ttc acc atc tct gat gtg ttt tcc aac tca act gat      672
Asp Glu Glu Leu Phe Thr Ile Ser Asp Val Phe Ser Asn Ser Thr Asp
        210                 215                 220 cac ttc acc aag gtg cta gac gtt gta att gct ctg ctc aat tct gtc      720
His Phe Thr Lys Val Leu Asp Val Val Ile Ala Leu Leu Asn Ser Val
225                 230                 235                 240 cct cag att ttc ttc aag ctg ccc tcc ccc aca atg gag gag cca cag      768
Pro Gln Ile Phe Phe Lys Leu Pro Ser Pro Thr Met Glu Glu Pro Gln
                245                 250                 255 gtc aat ggc tat tta tcc gat cat aac aaa att gtt aag gag ttc gtg      816
Val Asn Gly Tyr Leu Ser Asp His Asn Lys Ile Val Lys Glu Phe Val
            260                 265                 270 gaa aca gag cgg aag tac gtt cac gat ctg gaa gtc cta agc aaa tac      864
Glu Thr Glu Arg Lys Tyr Val His Asp Leu Glu Val Leu Ser Lys Tyr
            275                 280                 285 aga caa caa cta ttg gag aat cag att atc tcc tct gaa gag cta tac      912
Arg Gln Gln Leu Leu Glu Asn Gln Ile Ile Ser Ser Glu Glu Leu Tyr
        290                 295                 300 atg ctt ttc ccg aac ttg aat gag atc ata gac ttt caa agg aga ttt      960
Met Leu Phe Pro Asn Leu Asn Glu Ile Ile Asp Phe Gln Arg Arg Phe
305                 310                 315                 320 ctg gtt gct cta gaa att aac ggg cag gtt cct gcg caa gca caa cgg     1008
Leu Val Ala Leu Glu Ile Asn Gly Gln Val Pro Ala Gln Ala Gln Arg
                325                 330                 335 att ggt gct ctt ttt atg cat tcg aag cac ttc ttc aag ctt tat gag     1056
Ile Gly Ala Leu Phe Met His Ser Lys His Phe Phe Lys Leu Tyr Glu
            340                 345                 350 ccg tgg tct att ggg caa aat gcc gca att aat ttc atc tcg tcc agt     1104
Pro Trp Ser Ile Gly Gln Asn Ala Ala Ile Asn Phe Ile Ser Ser Ser
            355                 360                 365 ttt gac aag atg cag tcc caa gag ttt gtt ata ggc aac aaa atg gaa     1152
Phe Asp Lys Met Gln Ser Gln Glu Phe Val Ile Gly Asn Lys Met Glu
        370                 375                 380 ctg caa tcc ttt ctc cta aag ccg gtt caa agg ctg tgc cga tac cca     1200
Leu Gln Ser Phe Leu Leu Lys Pro Val Gln Arg Leu Cys Arg Tyr Pro
```

```
                385                 390                 395                 400
ctg ctg ctc aag gat ctt tta aaa ctc tct gtg aaa aca aaa agc gat       1248
Leu Leu Leu Lys Asp Leu Leu Lys Leu Ser Val Lys Thr Lys Ser Asp
                    405                 410                 415 gtg gac act aag gag tta caa act gct ctg gag att tct aaa tct att       1296
Val Asp Thr Lys Glu Leu Gln Thr Ala Leu Glu Ile Ser Lys Ser Ile
                420                 425                 430 gcc aga agt ata aat gaa aac caa agg cgc acg gag aat cat gag gtg       1344
Ala Arg Ser Ile Asn Glu Asn Gln Arg Arg Thr Glu Asn His Glu Val
            435                 440                 445 gtt aag aag ttg tat ggt cga gtg gta aac tgg aag ggc tat cgt att       1392
Val Lys Lys Leu Tyr Gly Arg Val Val Asn Trp Lys Gly Tyr Arg Ile
        450                 455                 460 gct aaa ttt ggc gaa ctt tta tat ttt gat aag gtg aac att tca aca       1440
Ala Lys Phe Gly Glu Leu Leu Tyr Phe Asp Lys Val Asn Ile Ser Thr
465                 470                 475                 480 agc aat tca aac gaa cct gaa aaa gaa ttt gaa gtt tat ttg ttt gaa       1488
Ser Asn Ser Asn Glu Pro Glu Lys Glu Phe Glu Val Tyr Leu Phe Glu
                485                 490                 495 aaa ata atc ata ctc ttt agt gag gtg caa caa aag aag tca aac tct       1536
Lys Ile Ile Ile Leu Phe Ser Glu Val Gln Gln Lys Lys Ser Asn Ser
                    500                 505                 510 cgg agt ttg aaa att aaa act aat tct atc tct tcc tcg tcc ttg cac       1584
Arg Ser Leu Lys Ile Lys Thr Asn Ser Ile Ser Ser Ser Ser Leu His
                515                 520                 525 cta tct gga gca aac tcc ccg tcc tct agc gct gtc agt ctg act gga       1632
Leu Ser Gly Ala Asn Ser Pro Ser Ser Ser Ala Val Ser Leu Thr Gly
            530                 535                 540 gat tcc aag tta gat ctg cgg ggc cgt att atg ata gta aat ctg atc       1680
Asp Ser Lys Leu Asp Leu Arg Gly Arg Ile Met Ile Val Asn Leu Ile
545                 550                 555                 560 cag att att ccg atc gaa aat cac tcg ttg aat atc act tgg gaa tca       1728
Gln Ile Ile Pro Ile Glu Asn His Ser Leu Asn Ile Thr Trp Glu Ser
                565                 570                 575 gcc aaa gag cag ggc aat ttc att cta aaa ttt aag aat gaa gag acc       1776
Ala Lys Glu Gln Gly Asn Phe Ile Leu Lys Phe Lys Asn Glu Glu Thr
                580                 585                 590 aga gat aat tgg tcg tct tgt ctc cag aat ctg cta cgc cag att agg       1824
Arg Asp Asn Trp Ser Ser Cys Leu Gln Asn Leu Leu Arg Gln Ile Arg
            595                 600                 605 agc gaa tct tat aaa tct acg gct acg ggt agt act gat cgc tct tca       1872
Ser Glu Ser Tyr Lys Ser Thr Ala Thr Gly Ser Thr Asp Arg Ser Ser
        610                 615                 620 ttc tcc tct ccg tat gga cac ccg cat tat agt gct gct tcc atc aac       1920
Phe Ser Ser Pro Tyr Gly His Pro His Tyr Ser Ala Ala Ser Ile Asn
625                 630                 635                 640 agc agt gct gta aga caa ata tca gaa gtg atg cct aaa cag ctc aat       1968
Ser Ser Ala Val Arg Gln Ile Ser Glu Val Met Pro Lys Gln Leu Asn
                645                 650                 655 cat cac cag acc ttt gag cac gag tac aga tcc ata tct gaa aac tac       2016
His His Gln Thr Phe Glu His Glu Tyr Arg Ser Ile Ser Glu Asn Tyr
                660                 665                 670 aag aat tct atc cca gaa tcc atg ttg atg gta cgg gta tca ttc aac       2064
Lys Asn Ser Ile Pro Glu Ser Met Leu Met Val Arg Val Ser Phe Asn
            675                 680                 685 aac gat ttc tac act ttg ctg gta tct atg gaa gcc gaa att gat gac       2112
Asn Asp Phe Tyr Thr Leu Leu Val Ser Met Glu Ala Glu Ile Asp Asp
        690                 695                 700 gtt cta gtt atg ctc aag aag aag tta gcc cac gca ggg tcc att tgt       2160
```

-continued

| | | | | | | | | | | | | | | |
|---|---|---|---|---|---|---|---|---|---|---|---|---|---|---|
|Val|Leu|Val|Met|Leu|Lys|Lys|Leu|Ala|His|Ala|Gly|Ser|Ile|Cys|
|705| | | | |710| | | |715| | | | |720|

```
aaa ata aag tat caa gat gag gat ggc gac ttc gtg atg ttg gag agt    2208
Lys Ile Lys Tyr Gln Asp Glu Asp Gly Asp Phe Val Met Leu Glu Ser
            725                 730                 735 gaa gac gat tgg tca gtt gtt aaa gat atg tta aag gag agc aaa gaa    2256
Glu Asp Asp Trp Ser Val Val Lys Asp Met Leu Lys Glu Ser Lys Glu
        740                 745                 750 cgg ata cta aac gtt tgg gca ttt gtt tga                            2286
Arg Ile Leu Asn Val Trp Ala Phe Val
        755                 760
```

<210> SEQ ID NO 14
<211> LENGTH: 761
<212> TYPE: PRT
<213> ORGANISM: Ashbya gossypii

<400> SEQUENCE: 14

```
Met Ser Asn Gln Ala Ser Gln Ser Thr Ile Ser Leu Arg Ser Val Val
  1               5                  10                  15

Ser Thr Ala Thr Gln Gln Leu Met Asn Lys Val Ser Glu Glu Asp
             20                  25                  30

Ser Leu Tyr His Ile Cys Val Gly Val Lys Arg Lys Leu Glu Cys Leu
             35                  40                  45

Pro Gln Leu Lys Pro Tyr Leu Ala Leu Ala His Ala Asn Ala Ala Leu
     50                  55                  60

Ala Ser Glu Gln Gln Ala Val Leu Leu Ala Gln Lys Asp Ala Met Glu
 65                  70                  75                  80

Ala Ala Glu Val Pro Leu Ser Pro Leu Asn Pro Ala His Asn Ser Met
                 85                  90                  95

Ile Ser Ala Ser Ala Gly Ala Ala Thr Ser Pro Val Ser Glu Ile Arg
            100                 105                 110

Pro Thr Ser Ile Ser Ser Ser Thr Leu Asp Glu Ser Glu Asp Ser Asn
            115                 120                 125

Ala Val Asn Met Glu Asp Thr Val Leu Thr Phe Ala Met Gly Ile Leu
        130                 135                 140

Pro Ser Ser Val Glu Cys Asp Pro Val Thr Glu Leu Ser Lys Leu Phe
145                 150                 155                 160

Gln Gln Gly Ser Pro Leu Cys Ile Ile Phe Asn Ala Val Lys Pro His
                165                 170                 175

Cys Lys Leu Pro Val Val Ser Ser Asp Thr Lys Ile Cys Lys Lys
            180                 185                 190

Ser Ile Tyr Asp Phe Ile Met Gly Leu Lys Leu His Phe Ala Phe Asn
            195                 200                 205

Asp Glu Glu Leu Phe Thr Ile Ser Asp Val Phe Ser Asn Ser Thr Asp
        210                 215                 220

His Phe Thr Lys Val Leu Asp Val Val Ile Ala Leu Leu Asn Ser Val
225                 230                 235                 240

Pro Gln Ile Phe Phe Lys Leu Pro Ser Pro Thr Met Glu Glu Pro Gln
                245                 250                 255

Val Asn Gly Tyr Leu Ser Asp His Asn Lys Ile Val Lys Glu Phe Val
            260                 265                 270

Glu Thr Glu Arg Lys Tyr Val His Asp Leu Glu Val Leu Ser Lys Tyr
        275                 280                 285

Arg Gln Gln Leu Leu Glu Asn Gln Ile Ile Ser Ser Glu Glu Leu Tyr
    290                 295                 300
```

```
Met Leu Phe Pro Asn Leu Asn Glu Ile Ile Asp Phe Gln Arg Arg Phe
305                 310                 315                 320

Leu Val Ala Leu Glu Ile Asn Gly Gln Val Pro Ala Gln Ala Gln Arg
            325                 330                 335

Ile Gly Ala Leu Phe Met His Ser Lys His Phe Lys Leu Tyr Glu
            340                 345                 350

Pro Trp Ser Ile Gly Gln Asn Ala Ala Ile Asn Phe Ile Ser Ser Ser
            355                 360                 365

Phe Asp Lys Met Gln Ser Gln Glu Phe Val Ile Gly Asn Lys Met Glu
370                 375                 380

Leu Gln Ser Phe Leu Leu Lys Pro Val Gln Arg Leu Cys Arg Tyr Pro
385                 390                 395                 400

Leu Leu Leu Lys Asp Leu Leu Lys Leu Ser Val Lys Thr Lys Ser Asp
                405                 410                 415

Val Asp Thr Lys Glu Leu Gln Thr Ala Leu Glu Ile Ser Lys Ser Ile
            420                 425                 430

Ala Arg Ser Ile Asn Glu Asn Gln Arg Arg Thr Glu Asn His Glu Val
        435                 440                 445

Val Lys Lys Leu Tyr Gly Arg Val Val Asn Trp Lys Gly Tyr Arg Ile
        450                 455                 460

Ala Lys Phe Gly Glu Leu Leu Tyr Phe Asp Lys Val Asn Ile Ser Thr
465                 470                 475                 480

Ser Asn Ser Asn Glu Pro Glu Lys Glu Phe Glu Val Tyr Leu Phe Glu
            485                 490                 495

Lys Ile Ile Ile Leu Phe Ser Glu Val Gln Gln Lys Lys Ser Asn Ser
            500                 505                 510

Arg Ser Leu Lys Ile Lys Thr Asn Ser Ile Ser Ser Ser Ser Leu His
        515                 520                 525

Leu Ser Gly Ala Asn Ser Pro Ser Ser Ser Ala Val Ser Leu Thr Gly
        530                 535                 540

Asp Ser Lys Leu Asp Leu Arg Gly Arg Ile Met Ile Val Asn Leu Ile
545                 550                 555                 560

Gln Ile Ile Pro Ile Glu Asn His Ser Leu Asn Ile Thr Trp Glu Ser
                565                 570                 575

Ala Lys Glu Gln Gly Asn Phe Ile Leu Lys Phe Lys Asn Glu Glu Thr
            580                 585                 590

Arg Asp Asn Trp Ser Ser Cys Leu Gln Asn Leu Leu Arg Gln Ile Arg
        595                 600                 605

Ser Glu Ser Tyr Lys Ser Thr Ala Thr Gly Ser Thr Asp Arg Ser Ser
        610                 615                 620

Phe Ser Ser Pro Tyr Gly His Pro His Tyr Ser Ala Ala Ser Ile Asn
625                 630                 635                 640

Ser Ser Ala Val Arg Gln Ile Ser Glu Val Met Pro Lys Gln Leu Asn
            645                 650                 655

His His Gln Thr Phe Glu His Gly Tyr Arg Ser Ile Ser Glu Asn Tyr
            660                 665                 670

Lys Asn Ser Ile Pro Glu Ser Met Leu Met Val Arg Val Ser Phe Asn
        675                 680                 685

Asn Asp Phe Tyr Thr Leu Leu Val Ser Met Glu Ala Glu Ile Asp Asp
        690                 695                 700

Val Leu Val Met Leu Lys Lys Lys Leu Ala His Ala Gly Ser Ile Cys
705                 710                 715                 720
```

```
Lys Ile Lys Tyr Gln Asp Glu Asp Gly Asp Phe Val Met Leu Glu Ser
                725                 730                 735
Glu Asp Asp Trp Ser Val Val Lys Asp Met Leu Lys Glu Ser Lys Glu
            740                 745                 750
Arg Ile Leu Asn Val Trp Ala Phe Val
        755                 760

<210> SEQ ID NO 15
<211> LENGTH: 576
<212> TYPE: DNA
<213> ORGANISM: Ashbya gossypii
<220> FEATURE:
<221> NAME/KEY: CDS
<222> LOCATION: (1)..(576)

<400> SEQUENCE: 15 atg cag aca ttg aag tgc gtg gtc gtt ggg gac gga gct gtc ggc aag        48
Met Gln Thr Leu Lys Cys Val Val Val Gly Asp Gly Ala Val Gly Lys
  1               5                  10                  15 aca tgc ttg ctc atc tcg tac acg acc aac cag ttt ccg gcg gac tac        96
Thr Cys Leu Leu Ile Ser Tyr Thr Thr Asn Gln Phe Pro Ala Asp Tyr
                 20                  25                  30 gtg ccc acg gtg ttc gac aac tac gcg gtg aca gtg atg atc ggg gac       144
Val Pro Thr Val Phe Asp Asn Tyr Ala Val Thr Val Met Ile Gly Asp
             35                  40                  45 gag ccg tac acg ttg ggc ttg ttc gac act gcc ggg cag gag gac tac       192
Glu Pro Tyr Thr Leu Gly Leu Phe Asp Thr Ala Gly Gln Glu Asp Tyr
         50                  55                  60 gac agg ttg cgg ccg ttg tcg tac ccg tcg acg gac gtg ttt ctc gtg       240
Asp Arg Leu Arg Pro Leu Ser Tyr Pro Ser Thr Asp Val Phe Leu Val
 65                  70                  75                  80 tgc ttc agc gtg gtt tca ccg ccg tcg ttc gag aac gtc aag gag aag       288
Cys Phe Ser Val Val Ser Pro Pro Ser Phe Glu Asn Val Lys Glu Lys
                 85                  90                  95 tgg ttc ccc gag gta cat cac cac tgc ccg ggc gta ccc tgc ttg att       336
Trp Phe Pro Glu Val His His His Cys Pro Gly Val Pro Cys Leu Ile
            100                 105                 110 gtc ggc acc cag ata gat ctc aga gag aac aaa atg gtc att gag aag       384
Val Gly Thr Gln Ile Asp Leu Arg Glu Asn Lys Met Val Ile Glu Lys
        115                 120                 125 cta cag aga cag cgg ctc cgc ccc atc acc ccc gag cag ggc gag aag       432
Leu Gln Arg Gln Arg Leu Arg Pro Ile Thr Pro Glu Gln Gly Glu Lys
    130                 135                 140 ttc gcg cgc gag ctc cgc gcc gtc aag tac gtg gag tgc tcg gcc ttg       480
Phe Ala Arg Glu Leu Arg Ala Val Lys Tyr Val Glu Cys Ser Ala Leu
145                 150                 155                 160 acc cag cgc ggc ttg aag aac gtc ttt gac gag gca att gtc gcc gcc       528
Thr Gln Arg Gly Leu Lys Asn Val Phe Asp Glu Ala Ile Val Ala Ala
                165                 170                 175 ctc gaa ccg ccg gtc atc aag aag agc aag aag tgc acc atc ttg tga       576
Leu Glu Pro Pro Val Ile Lys Lys Ser Lys Lys Cys Thr Ile Leu
            180                 185                 190

<210> SEQ ID NO 16
<211> LENGTH: 191
<212> TYPE: PRT
<213> ORGANISM: Ashbya gossypii

<400> SEQUENCE: 16

Met Gln Thr Leu Lys Cys Val Val Val Gly Asp Gly Ala Val Gly Lys
  1               5                  10                  15
```

```
Thr Cys Leu Leu Ile Ser Tyr Thr Thr Asn Gln Phe Pro Ala Asp Tyr
             20                  25                  30

Val Pro Thr Val Phe Asp Asn Tyr Ala Val Thr Val Met Ile Gly Asp
         35                  40                  45

Glu Pro Tyr Thr Leu Gly Leu Phe Asp Thr Ala Gly Gln Glu Asp Tyr
     50                  55                  60

Asp Arg Leu Arg Pro Leu Ser Tyr Pro Ser Thr Asp Val Phe Leu Val
 65                  70                  75                  80

Cys Phe Ser Val Val Ser Pro Ser Phe Glu Asn Val Lys Glu Lys
                 85                  90                  95

Trp Phe Pro Glu Val His His His Cys Pro Gly Val Pro Cys Leu Ile
             100                 105                 110

Val Gly Thr Gln Ile Asp Leu Arg Glu Asn Lys Met Val Ile Glu Lys
             115                 120                 125

Leu Gln Arg Gln Arg Leu Arg Pro Ile Thr Pro Glu Gln Gly Glu Lys
     130                 135                 140

Phe Ala Arg Glu Leu Arg Ala Val Lys Tyr Val Glu Cys Ser Ala Leu
145                 150                 155                 160

Thr Gln Arg Gly Leu Lys Asn Val Phe Asp Glu Ala Ile Val Ala Ala
                 165                 170                 175

Leu Glu Pro Pro Val Ile Lys Lys Ser Lys Lys Cys Thr Ile Leu
             180                 185                 190

<210> SEQ ID NO 17
<211> LENGTH: 693
<212> TYPE: DNA
<213> ORGANISM: Ashbya gossypii
<220> FEATURE:
<221> NAME/KEY: CDS
<222> LOCATION: (1)..(693)

<400> SEQUENCE: 17 atg cct gca cca gac ccc gca aga aga gat gtc ctt atc agc aaa tca        48
Met Pro Ala Pro Asp Pro Ala Arg Arg Asp Val Leu Ile Ser Lys Ser
 1               5                  10                  15 ctc tcg tac ttg ctg cgg cat ggc gcg ttg aag gaa cag ctg ccc att        96
Leu Ser Tyr Leu Leu Arg His Gly Ala Leu Lys Glu Gln Leu Pro Ile
             20                  25                  30 gac tca gac gga tac gtg cct gtc agc gca gtg ctg gcg cac aac cgc       144
Asp Ser Asp Gly Tyr Val Pro Val Ser Ala Val Leu Ala His Asn Arg
         35                  40                  45 ctc aag tca cat cgg tgt tcg ttc tcg gac ctc caa cgc atc gtc gaa       192
Leu Lys Ser His Arg Cys Ser Phe Ser Asp Leu Gln Arg Ile Val Glu
     50                  55                  60 aac aac gag aag aag cgc ttt cac atg cgt cca ggg ccg gac ggc cag       240
Asn Asn Glu Lys Lys Arg Phe His Met Arg Pro Gly Pro Asp Gly Gln
 65                  70                  75                  80 gaa tat ata tgt gcg acc cag ggc cac acc att gag cag gtg ctt ccc       288
Glu Tyr Ile Cys Ala Thr Gln Gly His Thr Ile Glu Gln Val Leu Pro
                 85                  90                  95 tct gcg gac gtc ctg acc cag ttg atc gat ccc ggt gag ctc cct gcg       336
Ser Ala Asp Val Leu Thr Gln Leu Ile Asp Pro Gly Glu Leu Pro Ala
            100                 105                 110 cag ctc atc cac ggg act aat ctg cgc aac gcc gtg ctt att ctc gac       384
Gln Leu Ile His Gly Thr Asn Leu Arg Asn Ala Val Leu Ile Leu Asp
        115                 120                 125 tcc ggg tgc atc aag cga atg cag cgg aat cat gtc cac ctg tcg cat       432
Ser Gly Cys Ile Lys Arg Met Gln Arg Asn His Val His Leu Ser His
    130                 135                 140
```

```
ggc gtt act ggc aag gac tgc gtg atc agc ggt atg cgg ctt agt agc    480
Gly Val Thr Gly Lys Asp Cys Val Ile Ser Gly Met Arg Leu Ser Ser
145                 150                 155                 160 aca gtg cac ata tac ttg aac aca gag ggc atc ctg gat cat ttg cga    528
Thr Val His Ile Tyr Leu Asn Thr Glu Gly Ile Leu Asp His Leu Arg
                165                 170                 175 tta tac aag tct cga aat gac gtc tac ctc aca ccc tcg gat att cca    576
Leu Tyr Lys Ser Arg Asn Asp Val Tyr Leu Thr Pro Ser Asp Ile Pro
            180                 185                 190 gtg tct atg ttc aag aag gtg gtg gtt cga aca agc aga aac acc aaa    624
Val Ser Met Phe Lys Lys Val Val Val Arg Thr Ser Arg Asn Thr Lys
        195                 200                 205 gct gac gat gtt acg acg cta acc cag aga cta gag cag cta gat gtg    672
Ala Asp Asp Val Thr Thr Leu Thr Gln Arg Leu Glu Gln Leu Asp Val
    210                 215                 220 ccc ttc gaa atc agc gac tga                                        693
Pro Phe Glu Ile Ser Asp
225                 230

<210> SEQ ID NO 18
<211> LENGTH: 230
<212> TYPE: PRT
<213> ORGANISM: Ashbya gossypii

<400> SEQUENCE: 18

Met Pro Ala Pro Asp Pro Ala Arg Arg Asp Val Leu Ile Ser Lys Ser
1               5                   10                  15

Leu Ser Tyr Leu Leu Arg His Gly Ala Leu Lys Glu Gln Leu Pro Ile
                20                  25                  30

Asp Ser Asp Gly Tyr Val Pro Val Ser Ala Val Leu Ala His Asn Arg
            35                  40                  45

Leu Lys Ser His Arg Cys Ser Phe Ser Asp Leu Gln Arg Ile Val Glu
        50                  55                  60

Asn Asn Glu Lys Lys Arg Phe His Met Arg Pro Gly Pro Asp Gly Gln
65                  70                  75                  80

Glu Tyr Ile Cys Ala Thr Gln Gly His Thr Ile Glu Gln Val Leu Pro
                85                  90                  95

Ser Ala Asp Val Leu Thr Gln Leu Ile Asp Pro Gly Glu Leu Pro Ala
            100                 105                 110

Gln Leu Ile His Gly Thr Asn Leu Arg Asn Ala Val Leu Ile Leu Asp
        115                 120                 125

Ser Gly Cys Ile Lys Arg Met Gln Arg Asn His Val His Leu Ser His
130                 135                 140

Gly Val Thr Gly Lys Asp Cys Val Ile Ser Gly Met Arg Leu Ser Ser
145                 150                 155                 160

Thr Val His Ile Tyr Leu Asn Thr Glu Gly Ile Leu Asp His Leu Arg
                165                 170                 175

Leu Tyr Lys Ser Arg Asn Asp Val Tyr Leu Thr Pro Ser Asp Ile Pro
            180                 185                 190

Val Ser Met Phe Lys Lys Val Val Val Arg Thr Ser Arg Asn Thr Lys
        195                 200                 205

Ala Asp Asp Val Thr Thr Leu Thr Gln Arg Leu Glu Gln Leu Asp Val
    210                 215                 220

Pro Phe Glu Ile Ser Asp
225                 230
```

```
<210> SEQ ID NO 19
<211> LENGTH: 2190
<212> TYPE: DNA
<213> ORGANISM: Ashbya gossypii
<220> FEATURE:
<221> NAME/KEY: CDS
<222> LOCATION: (1)..(2190)

<400> SEQUENCE: 19 atg tcg ctg gtt aac agt cac tcg tct gcg agc gtg gaa aac gct gcg     48
Met Ser Leu Val Asn Ser His Ser Ser Ala Ser Val Glu Asn Ala Ala
 1               5                  10                  15 tac aac cta cac cgc gca ttc agc tct agc acg gag aac gtg ggg cac     96
Tyr Asn Leu His Arg Ala Phe Ser Ser Ser Thr Glu Asn Val Gly His
            20                  25                  30 atg acg ccc agc aac tcg tcg ccg ttg cac cac tcc acg gtg gta gcg    144
Met Thr Pro Ser Asn Ser Ser Pro Leu His His Ser Thr Val Val Ala
        35                  40                  45 atg ggg gcg gaa tcg caa ggg ggc ggc gca agc aat aac aac aac aac    192
Met Gly Ala Glu Ser Gln Gly Gly Gly Ala Ser Asn Asn Asn Asn Asn
    50                  55                  60 ccc gcg aac ccg ggc agc acg gcc aac aat aat agt aat aac gtc aac    240
Pro Ala Asn Pro Gly Ser Thr Ala Asn Asn Asn Ser Asn Asn Val Asn
65                  70                  75                  80 atg aac agc atc ggt ggc ggg gcg agc ttg ggt gcc ggt agt ggg gcc    288
Met Asn Ser Ile Gly Gly Gly Ala Ser Leu Gly Ala Gly Ser Gly Ala
                85                  90                  95 acc ggc agt att tcg gga acg aag ggc atg aac aac agc cat tcg ccg    336
Thr Gly Ser Ile Ser Gly Thr Lys Gly Met Asn Asn Ser His Ser Pro
            100                 105                 110 ctc cat att gcc acg atg ctg aac acc ttg tcg atg aac tcg aat ccg    384
Leu His Ile Ala Thr Met Leu Asn Thr Leu Ser Met Asn Ser Asn Pro
        115                 120                 125 cca tcc caa cag cag tcc aat gta cag ggc cct tac ttg gtg cgg ttg    432
Pro Ser Gln Gln Gln Ser Asn Val Gln Gly Pro Tyr Leu Val Arg Leu
    130                 135                 140 cag aat gtt ccg aag gac act acc ttg cgg gaa tgc cat gct ttg ttt    480
Gln Asn Val Pro Lys Asp Thr Thr Leu Arg Glu Cys His Ala Leu Phe
145                 150                 155                 160 gca ttg gcg cac ggc gtg tta tct atc gag ttg tcg agc ttc cag cag    528
Ala Leu Ala His Gly Val Leu Ser Ile Glu Leu Ser Ser Phe Gln Gln
                165                 170                 175 tac gcc gag cga tct cag acg tct ggc cag gag tcc aca aat tac atc    576
Tyr Ala Glu Arg Ser Gln Thr Ser Gly Gln Glu Ser Thr Asn Tyr Ile
            180                 185                 190 gtt gcc aaa ttc gat tct ttg cat ttg gcg tgc cag tat gcg act att    624
Val Ala Lys Phe Asp Ser Leu His Leu Ala Cys Gln Tyr Ala Thr Ile
        195                 200                 205 ctt gat gag aag gct cag ata ttc ggg ccc agc ttt ccg ttc aaa acc    672
Leu Asp Glu Lys Ala Gln Ile Phe Gly Pro Ser Phe Pro Phe Lys Thr
    210                 215                 220 tac gtt gaa gtg gtt gac gag ctc acg caa cag cag ata ccg ttc cag    720
Tyr Val Glu Val Val Asp Glu Leu Thr Gln Gln Gln Ile Pro Phe Gln
225                 230                 235                 240 act caa atg caa atg cac cag ggc tcc cca cca gcc ccc acc cat gtc    768
Thr Gln Met Gln Met His Gln Gly Ser Pro Pro Ala Pro Thr His Val
                245                 250                 255 act gca tat caa cag cct ttg cta tct gct tcc ggc gtg gtt agc cca    816
Thr Ala Tyr Gln Gln Pro Leu Leu Ser Ala Ser Gly Val Val Ser Pro
            260                 265                 270 ccg caa tca gct tct agt gtg aag aga ccc agc ctt ttg gtc caa cgt    864
```

```
Pro Gln Ser Ala Ser Ser Val Lys Arg Pro Ser Leu Leu Val Gln Arg
            275                 280                 285 tcc agg ttc tca ttc acg gat ccg ttt tct agc gag caa act aat atg      912
Ser Arg Phe Ser Phe Thr Asp Pro Phe Ser Ser Glu Gln Thr Asn Met
    290                 295                 300 ggc tca cag cag cca gat cta att acg acg ccg ttg aaa ggt cac cag      960
Gly Ser Gln Gln Pro Asp Leu Ile Thr Thr Pro Leu Lys Gly His Gln
305                 310                 315                 320 gac act ggg aag tcg ttt tta ttg atg gaa agt gat gag att aac gat     1008
Asp Thr Gly Lys Ser Phe Leu Leu Met Glu Ser Asp Glu Ile Asn Asp
                325                 330                 335 agt ata tgg ggt aat gga acc ggc att cct tcc agc ata agt ggt ttg     1056
Ser Ile Trp Gly Asn Gly Thr Gly Ile Pro Ser Ser Ile Ser Gly Leu
            340                 345                 350 acg act tcg cag cca cca act cct cac ttg gag tgg ggt acc acg gga     1104
Thr Thr Ser Gln Pro Pro Thr Pro His Leu Glu Trp Gly Thr Thr Gly
            355                 360                 365 agg cgc caa agt tca act ttt tat cct tcg cag tcg aac aca gaa ata     1152
Arg Arg Gln Ser Ser Thr Phe Tyr Pro Ser Gln Ser Asn Thr Glu Ile
370                 375                 380 cca cct atg cat tta acg ggt caa gtg caa tct tca caa cta gca act     1200
Pro Pro Met His Leu Thr Gly Gln Val Gln Ser Ser Gln Leu Ala Thr
385                 390                 395                 400 ggt ttg caa caa ccg cta cca cag ccg caa cgt cag tct ttg tca tat     1248
Gly Leu Gln Gln Pro Leu Pro Gln Pro Gln Arg Gln Ser Leu Ser Tyr
                405                 410                 415 aac ttg gta aca ccg cta tcc tcc gat atg aac ttg cca cct cag tct     1296
Asn Leu Val Thr Pro Leu Ser Ser Asp Met Asn Leu Pro Pro Gln Ser
            420                 425                 430 tca cag ggc ggc ata tta ccg cat cag gcg cca gcg cag acg cag cca     1344
Ser Gln Gly Gly Ile Leu Pro His Gln Ala Pro Ala Gln Thr Gln Pro
            435                 440                 445 caa tcc caa gca ctc cag cat cac cag cat ttg cat cac cag cag cag     1392
Gln Ser Gln Ala Leu Gln His His Gln His Leu His His Gln Gln Gln
            450                 455                 460 caa ctc cag cag cag cag cac cac ctc cag cag cag cag cac cag cag     1440
Gln Leu Gln Gln Gln Gln His His Leu Gln Gln Gln Gln His Gln Gln
465                 470                 475                 480 cag caa cag tct ctt tca cag cag cca caa cag cag cag tct caa caa     1488
Gln Gln Gln Ser Leu Ser Gln Gln Pro Gln Gln Gln Gln Ser Gln Gln
                485                 490                 495 tcg cag gct cat tca caa cag cac cag cag cac caa cag cag cag         1536
Ser Gln Ala His Ser Gln Gln His Gln Gln His Gln Gln Gln Gln
            500                 505                 510 cag cag cag caa cct caa cag caa caa cca caa caa cat ccg ccg caa     1584
Gln Gln Gln Gln Pro Gln Gln Gln Gln Pro Gln Gln His Pro Pro Gln
            515                 520                 525 caa cct cag caa cag aat tct cag caa gcc atc gtt ggt cag tca cag     1632
Gln Pro Gln Gln Gln Asn Ser Gln Gln Ala Ile Val Gly Gln Ser Gln
        530                 535                 540 cag cag gta aca tcc gga cag cag aag ggt agc agc aga aat agc atc     1680
Gln Gln Val Thr Ser Gly Gln Gln Lys Gly Ser Ser Arg Asn Ser Ile
545                 550                 555                 560 tca aaa act tta caa gtc aac ggc cct aaa aat gct gct gca gct ttg     1728
Ser Lys Thr Leu Gln Val Asn Gly Pro Lys Asn Ala Ala Ala Ala Leu
                565                 570                 575 caa aat act aat ggt att tca caa gtt gat tta tct ttg ttg gct aaa     1776
Gln Asn Thr Asn Gly Ile Ser Gln Val Asp Leu Ser Leu Leu Ala Lys
            580                 585                 590
```

```
gtt cct cct ccc gca aat cca gct gat cag aac ccc cct tgt aac act    1824
Val Pro Pro Pro Ala Asn Pro Ala Asp Gln Asn Pro Pro Cys Asn Thr
        595                 600                 605 ctc tat gtt ggt aac ttg ccg cca gat gca act gaa caa gaa ttg cgc    1872
Leu Tyr Val Gly Asn Leu Pro Pro Asp Ala Thr Glu Gln Glu Leu Arg
610                 615                 620 cag tta ttc tct agt cag aag gga ttc agg aga ttg tca ttt agg aat    1920
Gln Leu Phe Ser Ser Gln Lys Gly Phe Arg Arg Leu Ser Phe Arg Asn
625                 630                 635                 640 aaa aat aac aac ggt aat ggc cat ggt cca atg tgc ttt gtt gag ttc    1968
Lys Asn Asn Asn Gly Asn Gly His Gly Pro Met Cys Phe Val Glu Phe
                645                 650                 655 gag gac gtt gcg cat gca acg agg gca ttg gct gaa tta tac ggt agt    2016
Glu Asp Val Ala His Ala Thr Arg Ala Leu Ala Glu Leu Tyr Gly Ser
            660                 665                 670 caa ttg gcg cgt aca agc ggc acc cac aat aat aaa ggt gga att agg    2064
Gln Leu Ala Arg Thr Ser Gly Thr His Asn Asn Lys Gly Gly Ile Arg
        675                 680                 685 ttg agt ttc tct aag aac cca ttg ggt gtc agg ggt ccc aac agc aga    2112
Leu Ser Phe Ser Lys Asn Pro Leu Gly Val Arg Gly Pro Asn Ser Arg
690                 695                 700 aga ggt ggt gct acc aat aac act tcc aat gcc ggc acg aca aac tac    2160
Arg Gly Gly Ala Thr Asn Asn Thr Ser Asn Ala Gly Thr Thr Asn Tyr
705                 710                 715                 720 tca tac gca gct gcc ttc ggc aaa tct tga                            2190
Ser Tyr Ala Ala Ala Phe Gly Lys Ser
                725                 730

<210> SEQ ID NO 20
<211> LENGTH: 729
<212> TYPE: PRT
<213> ORGANISM: Ashbya gossypii

<400> SEQUENCE: 20

Met Ser Leu Val Asn Ser His Ser Ser Ala Ser Val Glu Asn Ala Ala
 1               5                  10                  15

Tyr Asn Leu His Arg Ala Phe Ser Ser Thr Glu Asn Val Gly His
            20                  25                  30

Met Thr Pro Ser Asn Ser Ser Pro Leu His His Ser Thr Val Val Ala
        35                  40                  45

Met Gly Ala Glu Ser Gln Gly Gly Ala Ser Asn Asn Asn Asn
    50                  55                  60

Pro Ala Asn Pro Gly Ser Thr Ala Asn Asn Ser Asn Asn Val Asn
65                  70                  75                  80

Met Asn Ser Ile Gly Gly Ala Ser Leu Gly Ala Gly Ser Gly Ala
                85                  90                  95

Thr Gly Ser Ile Ser Gly Thr Lys Gly Met Asn Asn Ser His Ser Pro
            100                 105                 110

Leu His Ile Ala Thr Met Leu Asn Thr Leu Ser Met Asn Ser Asn Pro
        115                 120                 125

Pro Ser Gln Gln Gln Ser Asn Val Gln Gly Pro Tyr Leu Val Arg Leu
    130                 135                 140

Gln Asn Val Pro Lys Asp Thr Thr Leu Arg Glu Cys His Ala Leu Phe
145                 150                 155                 160

Ala Leu Ala His Gly Val Leu Ser Ile Glu Leu Ser Ser Phe Gln Gln
                165                 170                 175

Tyr Ala Glu Arg Ser Gln Thr Ser Gly Gln Glu Ser Thr Asn Tyr Ile
            180                 185                 190
```

```
Val Ala Lys Phe Asp Ser Leu His Leu Ala Cys Gln Tyr Ala Thr Ile
            195                 200                 205

Leu Asp Glu Lys Ala Gln Ile Phe Gly Pro Ser Phe Pro Phe Lys Thr
            210                 215                 220

Tyr Val Glu Val Val Asp Glu Leu Thr Gln Gln Ile Pro Phe Gln
225                 230                 235                 240

Thr Gln Met Gln Met His Gln Gly Ser Pro Pro Ala Pro Thr His Val
                245                 250                 255

Thr Ala Tyr Gln Gln Pro Leu Leu Ser Ala Ser Gly Val Val Ser Pro
                260                 265                 270

Pro Gln Ser Ala Ser Ser Val Lys Arg Pro Ser Leu Leu Val Gln Arg
            275                 280                 285

Ser Arg Phe Ser Phe Thr Asp Pro Phe Ser Ser Glu Gln Thr Asn Met
            290                 295                 300

Gly Ser Gln Gln Pro Asp Leu Ile Thr Thr Pro Leu Lys Gly His Gln
305                 310                 315                 320

Asp Thr Gly Lys Ser Phe Leu Leu Met Glu Ser Asp Glu Ile Asn Asp
                325                 330                 335

Ser Ile Trp Gly Asn Gly Thr Gly Ile Pro Ser Ser Ile Ser Gly Leu
                340                 345                 350

Thr Thr Ser Gln Pro Pro Thr Pro His Leu Glu Trp Gly Thr Thr Gly
            355                 360                 365

Arg Arg Gln Ser Ser Thr Phe Tyr Pro Ser Gln Ser Asn Thr Glu Ile
            370                 375                 380

Pro Pro Met His Leu Thr Gly Gln Val Gln Ser Ser Gln Leu Ala Thr
385                 390                 395                 400

Gly Leu Gln Gln Pro Leu Pro Gln Pro Gln Arg Gln Ser Leu Ser Tyr
                405                 410                 415

Asn Leu Val Thr Pro Leu Ser Ser Asp Met Asn Leu Pro Pro Gln Ser
                420                 425                 430

Ser Gln Gly Gly Ile Leu Pro His Gln Ala Pro Ala Gln Thr Gln Pro
            435                 440                 445

Gln Ser Gln Ala Leu Gln His His Gln His Leu His Gln Gln Gln
            450                 455                 460

Gln Leu Gln Gln Gln Gln His His Leu Gln Gln Gln His Gln Gln
465                 470                 475                 480

Gln Gln Gln Ser Leu Ser Gln Gln Pro Gln Gln Gln Ser Gln Gln
                485                 490                 495

Ser Gln Ala His Ser Gln Gln His Gln Gln His Gln Gln Gln Gln
            500                 505                 510

Gln Gln Gln Gln Pro Gln Gln Gln Pro Gln Gln His Pro Pro Gln
            515                 520                 525

Gln Pro Gln Gln Gln Asn Ser Gln Ala Ile Val Gly Gln Ser Gln
            530                 535                 540

Gln Gln Val Thr Ser Gly Gln Gln Lys Gly Ser Ser Arg Asn Ser Ile
545                 550                 555                 560

Ser Lys Thr Leu Gln Val Asn Gly Pro Lys Asn Ala Ala Ala Leu
                565                 570                 575

Gln Asn Thr Asn Gly Ile Ser Gln Val Asp Leu Ser Leu Leu Ala Lys
                580                 585                 590

Val Pro Pro Pro Ala Asn Pro Ala Asp Gln Asn Pro Pro Cys Asn Thr
            595                 600                 605
```

```
Leu Tyr Val Gly Asn Leu Pro Pro Asp Ala Thr Glu Gln Glu Leu Arg
    610                 615                 620
Gln Leu Phe Ser Ser Gln Lys Gly Phe Arg Arg Leu Ser Phe Arg Asn
625                 630                 635                 640
Lys Asn Asn Asn Gly Asn Gly His Gly Pro Met Cys Phe Val Glu Phe
                645                 650                 655
Glu Asp Val Ala His Ala Thr Arg Ala Leu Ala Glu Leu Tyr Gly Ser
            660                 665                 670
Gln Leu Ala Arg Thr Ser Gly Thr His Asn Asn Lys Gly Ile Arg
        675                 680                 685
Leu Ser Phe Ser Lys Asn Pro Leu Gly Val Arg Gly Pro Asn Ser Arg
    690                 695                 700
Arg Gly Gly Ala Thr Asn Asn Thr Ser Asn Ala Gly Thr Thr Asn Tyr
705                 710                 715                 720
Ser Tyr Ala Ala Ala Phe Gly Lys Ser
                725
```

```
<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
gctagggata acagggtaat                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
aggcatgcaa gcttagatct                                               20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gtttagtctg accatctcat ctg                                           23

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
tcgcagaccg ataccaggat c                                             21

<210> SEQ ID NO 25
<211> LENGTH: 71
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
gaggctgtca actcgctcgc cactacgttt actggcacct cgtactacat ggctagggat    60
aacagggtaa t                                                          71

<210> SEQ ID NO 26
<211> LENGTH: 70
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
gagacagtag ctgatgaatg acttgaaggc cttgctccac acgatgttcg aggcatgcaa    60
gcttagatct                                                            70

<210> SEQ ID NO 27
<211> LENGTH: 65
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
ctccaacgag ccctgcaaca tagtggcagt agcggtcgta gtcctgctag ggataacagg    60
gtaat                                                                 65

<210> SEQ ID NO 28
<211> LENGTH: 65
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
cttttgcggc cgtgataatg gagctacatc ccgagctgcg caacgaggca tgcaagctta    60
gatct                                                                 65

<210> SEQ ID NO 29
<211> LENGTH: 70
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
cgttggaggt gcccagctca taccacgtcg gggagctgaa catgcgggag gctagggata    60
acagggtaat                                                            70

<210> SEQ ID NO 30
<211> LENGTH: 68
<212> TYPE: DNA
<213> ORGANISM: Artificial Sequence
<220> FEATURE:
<223> OTHER INFORMATION: Description of Artificial Sequence:
``` oligonucleotide

<400> SEQUENCE: 30
caggtatcgg aagaagtctg cgcgcatgat ggccagaggc agcgactcag gcatgcaagc    60
ttagatct                                                             68

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gtcacattcc gtggtgccac gaatttccgg cacagaatag tgatggccac gctagggata    60
acagggtaat                                                           70

<210> SEQ ID NO 32
<211> LENGTH: 71
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
cttgattgtg acgatcaggt cgtcggtgtc atcgtcagca ggtttcagca gaggcatgca    60
agcttagatc t                                                         71

<210> SEQ ID NO 33
<211> LENGTH: 65
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
cggacagcgt tcagagaaga cagagacaat caacaccaaa caaacgctag ggataacagg    60
gtaat                                                                65

<210> SEQ ID NO 34
<211> LENGTH: 65
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
agcagaactg acagatttga tacccgcacg gacacggctt aaagtaggca tgcaagctta    60
gatct                                                                65

<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35

```
cgtttgtggt tgccgcaata ctctttatct ttgcacctcc gaccacccttt aggctaggga    60 taacagggta at                                                          72
```

<210> SEQ ID NO 36
<211> LENGTH: 73
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36

```
cagcagagtt cgaaaacgca gttgtgtata gatcaatgcc caagtactca tcgaggcatg    60
caagcttaga tct                                                        73
```

<210> SEQ ID NO 37
<211> LENGTH: 68
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37

```
acttcttcaa gctttatgag ccgtggtcta ttgggcaaaa tgccgcaagc tagggataac    60
agggtaat                                                              68
```

<210> SEQ ID NO 38
<211> LENGTH: 69
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38

```
ggtatcggca cagcctttga accggcttta ggagaaagga ttgcagttca ggcatgcaag    60
cttagatct                                                             69
```

<210> SEQ ID NO 39
<211> LENGTH: 87
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39

```
gaggactacg acaggttgcg gccgttgtcg tacccgtcga cggacgtgtt tctcgtgtgc    60
ttcagcggct agggataaca gggtaat                                         87
```

<210> SEQ ID NO 40
<211> LENGTH: 87
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40

```
gcagggtacg cccgggcagt ggtgatgtac ctcggggaac cacttctcct tgacgttctc    60
gaacgacagg catgcaagct tagatct                                         87
```

```
<210> SEQ ID NO 41
<211> LENGTH: 70
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
gcatagaaaa tgcactacat gcaacagcag ggaccatgcc tgcaccagac gctagggata     60
acagggtaat                                                            70

<210> SEQ ID NO 42
<211> LENGTH: 70
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
gaacatagac actggaatat ccgagggtgt gaggtagacg tcatttcgag aggcatgcaa     60
gcttagatct                                                            70

<210> SEQ ID NO 43
<211> LENGTH: 66
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
ctcctcactt ggagtggggt accacgggaa ggcgccaaag ttcaacgcta gggataacag     60
ggtaat                                                                66

<210> SEQ ID NO 44
<211> LENGTH: 66
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
ctggtgatgc tggagtgctt gggattgtgg ctgcgtctgc gctggcaggc atgcaagctt     60
agatct                                                                66
```